(12) United States Patent
Santin

(10) Patent No.: US 8,097,242 B2
(45) Date of Patent: Jan. 17, 2012

(54) TARGET CA125 PEPTIDES FOR CANCER IMMUNOTHERAPY

(75) Inventor: Alessandro D. Santin, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 833 days.

(21) Appl. No.: 11/973,132

(22) Filed: Oct. 5, 2007

(65) Prior Publication Data

US 2008/0085266 A1 Apr. 10, 2008

Related U.S. Application Data

(60) Provisional application No. 60/849,721, filed on Oct. 5, 2006.

(51) Int. Cl.
A61K 48/00 (2006.01)
A61K 38/00 (2006.01)
(52) U.S. Cl. .......................... 424/93.1; 514/2
(58) Field of Classification Search ........................ None
See application file for complete search history.

(56) References Cited

U.S. PATENT DOCUMENTS

| | | | |
|---|---|---|---|
| 5,788,963 A * | 8/1998 | Murphy et al. | |
| 6,858,710 B2 * | 2/2005 | Bangur et al. | 530/386 |
| 2003/0143667 A1 * | 7/2003 | O'Brien et al. | |
| 2004/0127401 A1 | 7/2004 | O'Brien | |
| 2007/0015907 A1 | 1/2007 | O'Brien | |

FOREIGN PATENT DOCUMENTS

WO WO 99/65517 A2 12/1999

OTHER PUBLICATIONS

Rammensee et al. Immunogenetics, 41:178-228, 1995.*
Lazzarino et al. Cancer, 82(3):576-582, Feb. 1, 1998.*
Score search results, issued patent database, SEQ ID No:10, Mar. 14, 2011.*
Score search results, issued patent database, SEQ ID No:7, Mar. 14, 2011.*
Underwood LJ, Shigemasa K, Tanimoto H, Beard JB, Schneider EN, Wang Y, Parmley TH, O'Brien TJ. (2000) Ovarian tumor cells express a novel multi-domain cell surface serine protease. *Biochim Biophys Acta* 1502(3):337-50.
O'Brien, T.J., et al. (2002) the CA 125 gene: a newly discovered extension of the glycosylated N-terminal domain structure doubles the size of this extracellular superstructure. Tumor Biol. 23:154-169.
Parker, K. C., M. A. Bednarek, and J. E. Coligan. 1994. Scheme for ranking potential HLA-A2 binding peptides based on independent binding of individual peptide side-chains. J. Immunol. 152:163.
Santin AD. Hermonat PL. Ravaggi A. Bellone S. Roman JJ. Jayaprabhu S. Pecorelli S. Parham GP. Cannon MJ. (2001) Expression of CD56 by human papillomavirus E7-specific CD8+ cytotoxic T lymphocytes correlates with increased intracellular perforin expression and enhanced cytotoxicity against HLA-A2-matched cervical tumor cells. *Clin Cancer Res*. 7(3 Suppl):804s-810s.
Levitsky V, Zhang QJ, Levitskaya J, Masucci M.G. (1996) The life span of major histocompatibility complex-peptide complexes influences the efficiency of presentation and immunogenicity of two class I-restricted cytotoxic T lymphocyte epitopes in the Epstein-Barr virus nuclear antigen 4. J Exp Med. 183(3):915-26.
Torsteinsdottir S, Masucci MG, Ehlin-Henriksson B, Brautbar C, Ben Bassat H, Klein G, Klein E. (1986) Differentiation-dependent sensitivity of human B-cell-derived lines to major histocompatibility complex-restricted T-cell cytotoxicity. Proc Natl Acad Sci U S A. 83(15):5620-4.
Alexander, M.A., Damico, C.A., Wieties, K.M., Hansen, T.H. and Connolly J.M. (1991) Correlation between CD8 dependency and determinant density using peptide-induced, Ld-restricted cytotoxic T lymphocytes. J. Exp. Med. 173: 849-858.
Alexander-Miller, M.A., Leggatt, G.R. and Berzofsky, Y.A. (1996) Selective expansion of high- or low-avidity cytotoxic T lymphocytes and efficacy for adoptive immunotherapy. Proc. Nat. Acad. Sci. USA. 93: 4102-4107.
Ioannides CG, Whiteside TL. T cell recognition of human tumors: implications for molecular immunotherapy of cancer. Clin. Immunol. Immunopath. 1993;66:91-106.
Santin AD, Hermonat PL, Ravaggi A, Cannon MJ, Pecorelli S, and Parham GP. Secretion of vascular endothelial growth factor in ovarian cancer. Eur J Gynecol. Oncol 1999;3: 177-181.
Mulders P, Tso C-L, Gitlitz B, Kaboo R, Hinkel A, Frand S, et al. Presentation of renal tumor antigens by human dendritic cells activates tumor infiltrating lymphocytes against autologous tumor: implications for live kidney cancer vaccines. Clin Cancer Res 1999;5:445-454.
Santin AD, Hermonat PL, Ravaggi A, Chiriva-Internati M, Cannon MJ, Hiserodt JC, et al. Kinetics of expression of surface antigens during the differentiation of human dendritic cells versus macrophages from monocytes in vitro. Immunobiology 1999;200:187-204.
Steinman RA. The DC system and its role in immunogenicity. Ann. Rev. Immunol. 1991;9: 271-296.

(Continued)

*Primary Examiner* — Laura B Goddard
(74) *Attorney, Agent, or Firm* — Hugh McTavish

(57) ABSTRACT

TADG-12 and CA125 are two proteins expressed with high specificity in ovarian cancer tumors. They thus would be potential antigens for immunotherapy in ovarian cancer. The invention is based on the discovery of peptides in TADG-12 and CA125 that can be used to induce an autologous T cell response that lyses ovarian cancer cells expressing TADG-12 or CA125. The peptides are contacted with dendritic cells in vitro to generate peptide-loaded dendritic cells. The peptide-loaded dendritic cells are contacted with T cells in vitro to amplify CD8+ T cells that recognize the peptide. At least one CA125 peptide and at least one TADG-12 peptide were found that amplified CD8+ T cells, even from cancer patients, that lysed autologous CA125-expressing or TADG-12-expressing tumor cells. The peptide-loaded dendritic cells can be administered to a cancer patient to amplify CD8+ T cells in vivo that attack the cancer cells. Alternatively, autologous CD8+ T cells can be amplified ex vivo and then infused into the cancer patient.

17 Claims, 12 Drawing Sheets

OTHER PUBLICATIONS

Sallusto F, Lanzavecchia A. Efficient presentation of soluable antigen by cultured human dendritic cells is maintanined by granulocyte/macrophage colony stimulating factor plus interleukin 4 and down regulated by turner necrosis factor alpha. J Exp Med 1994;17:1109-1118.

Young JW, Inaba K. DCs as adjuvants for class I major histocompatibility complex-restricted antitumor immunity. J Exp Med 1996;183:7-11.

Schuler G, Steinman RM. Dendritic cells as adjuvants for immune-mediated resistance to tumors. J Exp Med 1997;186:1183-1187.

Banchereau J, Steinman RM. Dendritic cells and the control of immunity. Nature 1998;392:245-252.

Jonuleit H, Kuhn U, Muller G, Steinbrink K, Pragnik L, Schmitt, E, et al. Pro-inflammatory cytokines and prostaglandins induce maturation of potent immunostimulatory dendritic cells under fetal calf serum-free conditions. Eur J Immunol 1997;27:3135-3142.

Dhodapkar MV, Steinman RM, Sapp M, Desai H, Fossella C, Krasovsky J, et al. Rapid generation of broad T-cell immunity in humans after a single injection of mature dendritic cells. J Clin Invest 1999;104:173-180.

Dhodapkar MV, Krasovsky J, Steinman RM, Bhardwaj N. Mature dendritic cells boost functionally superior CD8+ T-cell in humans without foreign helper epitopes. J Clin Invest 2000;105:R9-R14.

Hsu FJ, Benike C, Fagnoni F Liles TM, Czerwinski D, Taidi B, et al. Vaccination of patients with B-cell lymphoma using autologous antigen-pulsed dendritic cells. Nature Med 1996;2,:52-58.

Geiger JD, Hutchinson RJ, Hohenkirk LF, McKenna EA, Yanik GA, Levine JE, et al. Vaccination of pediatric solid tumor patients with tumor lysate-pulsed dendritic cells can expand specific T cells and mediate tumor regression. Cancer Research. 2001;61:8513-8519.

Mellman, I. et al., 2001, Dendritic cells: specialized antigen-presenting machines. Cell 106:255-258.

Thurner, B et al., 1999, Vaccination with Mage-3A1 peptide-pulsed mature, monocyte-derived dendritic cells expands specific cytotoxic T cells and induces regression of some matastases in advanced stage IV melanoma. J.Exp. Med. 190:1669-1678.

Kugler, A et al., 2000, Regression of human metastatic renal cell carcinoma after vaccination with tumor cell-dendritic cell hybrids. Nature Medicine 6:332-336.

* cited by examiner

SEQUENCE LISTING

<160> NUMBER OF SEQ ID NOS: 22

<210> SEQ ID NO 1
<211> LENGTH: 9
<212> TYPE: PRT
<213> ORGANISM: Homo sapiens

<400> SEQUENCE: 1

Trp Leu Gly Ser Thr Tyr Gln Leu Val
1               5

<210> SEQ ID NO 2
<211> LENGTH: 9
<212> TYPE: PRT
<213> ORGANISM: Homo sapiens

<400> SEQUENCE: 2

Val Leu Phe Thr Leu Asn Phe Thr Ile
1               5

<210> SEQ ID NO 3
<211> LENGTH: 9
<212> TYPE: PRT
<213> ORGANISM: Homo sapiens

<400> SEQUENCE: 3

Leu Leu Asp Arg Gly Ser Leu Tyr Val
1               5

<210> SEQ ID NO 4
<211> LENGTH: 9
<212> TYPE: PRT
<213> ORGANISM: Homo sapiens

<400> SEQUENCE: 4

Tyr Leu Gly Cys Gln Leu Ile Ser Leu
1               5

<210> SEQ ID NO 5
<211> LENGTH: 9
<212> TYPE: PRT
<213> ORGANISM: Homo sapiens

<400> SEQUENCE: 5

Thr Leu Asn Ala Ser Phe His Trp Leu
1               5

<210> SEQ ID NO 6
<211> LENGTH: 9
<212> TYPE: PRT
<213> ORGANISM: Homo sapiens

<400> SEQUENCE: 6

Gly Val Thr Gln Leu Gly Phe Tyr Val
1               5

<210> SEQ ID NO 7
<211> LENGTH: 10
<212> TYPE: PRT
<213> ORGANISM: Homo sapiens

<400> SEQUENCE: 7

Tyr Leu Leu Asp Arg Gly Ser Leu Tyr Val
1               5                   10

```
<210> SEQ ID NO 8
<211> LENGTH: 10
<212> TYPE: PRT
<213> ORGANISM: Homo sapiens

<400> SEQUENCE: 8

Gln Leu His Asp Thr Phe Arg Phe Cys Leu
1               5                   10

<210> SEQ ID NO 9
<211> LENGTH: 10
<212> TYPE: PRT
<213> ORGANISM: Homo sapiens

<400> SEQUENCE: 9

Leu Leu Met Pro Phe Thr Leu Asn Phe Thr
1               5                   10

<210> SEQ ID NO 10
<211> LENGTH: 10
<212> TYPE: PRT
<213> ORGANISM: Homo sapiens

<400> SEQUENCE: 10

Tyr Thr Leu Asp Arg Asp Ser Leu Tyr Val
1               5                   10

<210> SEQ ID NO 11
<211> LENGTH: 10
<212> TYPE: PRT
<213> ORGANISM: Homo sapiens

<400> SEQUENCE: 11

Phe Met Val Pro Phe Thr Leu Asn Phe Thr
1               5                   10

<210> SEQ ID NO 12
<211> LENGTH: 10
<212> TYPE: PRT
<213> ORGANISM: Homo sapiens

<400> SEQUENCE: 12

Thr Leu Leu Val Thr Gly Thr Ser Arg Val
1               5                   10

<210> SEQ ID NO 13
<211> LENGTH: 9
<212> TYPE: PRT
<213> ORGANISM: Homo sapiens

<400> SEQUENCE: 13

Ala Gln Leu Gly Phe Pro Ser Tyr Val
1               5

<210> SEQ ID NO 14
<211> LENGTH: 9
<212> TYPE: PRT
<213> ORGANISM: Homo sapiens

<400> SEQUENCE: 14

Leu Leu Pro Leu Lys Phe Phe Pro Ile
1               5

<210> SEQ ID NO 15
```

-continued

```
<211> LENGTH: 10
<212> TYPE: PRT
<213> ORGANISM: Homo sapiens

<400> SEQUENCE: 15

Ser Leu Leu Pro Leu Lys Phe Phe Pro Ile
1               5                   10

<210> SEQ ID NO 16
<211> LENGTH: 10
<212> TYPE: PRT
<213> ORGANISM: Homo sapiens

<400> SEQUENCE: 16

Leu Leu Pro Asp Asp Lys Val Thr Ala Leu
1               5                   10

<210> SEQ ID NO 17
<211> LENGTH: 10
<212> TYPE: PRT
<213> ORGANISM: Homo sapiens

<400> SEQUENCE: 17

Tyr Leu Pro Lys Ser Trp Thr Ile Gln Val
1               5                   10

<210> SEQ ID NO 18
<211> LENGTH: 10
<212> TYPE: PRT
<213> ORGANISM: Homo sapiens

<400> SEQUENCE: 18

Gly Leu Asp Asp Leu Lys Ile Ser Pro Val
1               5                   10

<210> SEQ ID NO 19
<211> LENGTH: 10
<212> TYPE: PRT
<213> ORGANISM: Homo sapiens

<400> SEQUENCE: 19

Lys Leu Val Gly Ala Thr Ser Phe Gly Ile
1               5                   10

<210> SEQ ID NO 20
<211> LENGTH: 10
<212> TYPE: PRT
<213> ORGANISM: Homo sapiens

<400> SEQUENCE: 20

Ser Leu Leu Ser Gln Trp Pro Trp Gln Ala
1               5                   10

<210> SEQ ID NO 21
<211> LENGTH: 454
<212> TYPE: PRT
<213> ORGANISM: Homo sapiens

<400> SEQUENCE: 21

Met Gly Glu Asn Asp Pro Pro Ala Val Glu Ala Pro Phe Ser Phe Arg
1               5                   10                  15

Ser Leu Phe Gly Leu Asp Asp Leu Lys Ile Ser Pro Val Ala Pro Asp
                20                  25                  30

Ala Asp Ala Val Ala Ala Gln Ile Leu Ser Leu Leu Pro Leu Lys Phe
            35                  40                  45
```

```
Phe Pro Ile Ile Val Ile Gly Ile Ala Leu Ile Leu Ala Leu Ala
 50                  55                  60
Ile Gly Leu Gly Ile His Phe Asp Cys Ser Gly Lys Tyr Arg Cys Arg
65                   70                  75                  80
Ser Ser Phe Lys Cys Ile Glu Leu Ile Ala Arg Cys Asp Gly Val Ser
                 85                  90                  95
Asp Cys Lys Asp Gly Glu Asp Glu Tyr Arg Cys Val Arg Val Gly Gly
             100                 105                 110
Gln Asn Ala Val Leu Gln Val Phe Thr Ala Ala Ser Trp Lys Thr Met
             115                 120                 125
Cys Ser Asp Asp Trp Lys Gly His Tyr Ala Asn Val Ala Cys Ala Gln
             130                 135                 140
Leu Gly Phe Pro Ser Tyr Val Ser Ser Asp Asn Leu Arg Val Ser Ser
145                 150                 155                 160
Leu Glu Gly Gln Phe Arg Glu Glu Phe Val Ser Ile Asp His Leu Leu
                 165                 170                 175
Pro Asp Asp Lys Val Thr Ala Leu His His Ser Val Tyr Val Arg Glu
             180                 185                 190
Gly Cys Ala Ser Gly His Val Thr Leu Gln Cys Thr Ala Cys Gly
             195                 200                 205
His Arg Arg Gly Tyr Ser Ser Arg Ile Val Gly Gly Asn Met Ser Leu
210                 215                 220
Leu Ser Gln Trp Pro Trp Gln Ala Ser Leu Gln Phe Gln Gly Tyr His
225                 230                 235                 240
Leu Cys Gly Gly Ser Val Ile Thr Pro Leu Trp Ile Ile Thr Ala Ala
                 245                 250                 255
His Cys Val Tyr Asp Leu Tyr Leu Pro Lys Ser Trp Thr Ile Gln Val
             260                 265                 270
Gly Leu Val Ser Leu Leu Asp Asn Pro Ala Pro Ser His Leu Val Glu
             275                 280                 285
Lys Ile Val Tyr His Ser Lys Tyr Lys Pro Lys Arg Leu Gly Asn Asp
             290                 295                 300
Ile Ala Leu Met Lys Leu Ala Gly Pro Leu Thr Phe Asn Glu Met Ile
305                 310                 315                 320
Gln Pro Val Cys Leu Pro Asn Ser Glu Glu Asn Phe Pro Asp Gly Lys
                 325                 330                 335
Val Cys Trp Thr Ser Gly Trp Gly Ala Thr Glu Asp Gly Ala Gly Asp
             340                 345                 350
Ala Ser Pro Val Leu Asn His Ala Ala Val Pro Leu Ile Ser Asn Lys
             355                 360                 365
Ile Cys Asn His Arg Asp Val Tyr Gly Gly Ile Ile Ser Pro Ser Met
             370                 375                 380
Leu Cys Ala Gly Tyr Leu Thr Gly Gly Val Asp Ser Cys Gln Gly Asp
385                 390                 395                 400
Ser Gly Gly Pro Leu Val Cys Gln Glu Arg Arg Leu Trp Lys Leu Val
                 405                 410                 415
Gly Ala Thr Ser Phe Gly Ile Gly Cys Ala Glu Val Asn Lys Pro Gly
             420                 425                 430
Val Tyr Thr Arg Val Thr Ser Phe Leu Asp Trp Ile His Glu Gln Met
             435                 440                 445
Glu Arg Asp Leu Lys Thr
450
```

```
<210> SEQ ID NO 22
<211> LENGTH: 293
<212> TYPE: PRT
<213> ORGANISM: Homo sapiens

<400> SEQUENCE: 22

Met Gly Glu Asn Asp Pro Pro Ala Val Glu Ala Pro Phe Ser Phe Arg
1               5                   10                  15

Ser Leu Phe Gly Leu Asp Asp Leu Lys Ile Ser Pro Val Ala Pro Asp
            20                  25                  30

Ala Asp Ala Val Ala Ala Gln Ile Leu Ser Leu Leu Pro Leu Lys Phe
        35                  40                  45

Phe Pro Ile Ile Val Ile Gly Ile Ile Ala Leu Ile Leu Ala Leu Ala
    50                  55                  60

Ile Gly Leu Gly Ile His Phe Asp Cys Ser Gly Lys Tyr Arg Cys Arg
65                  70                  75                  80

Ser Ser Phe Lys Cys Ile Glu Leu Ile Ala Arg Cys Asp Gly Val Ser
                85                  90                  95

Asp Cys Lys Asp Gly Glu Asp Glu Tyr Arg Cys Val Arg Val Gly Gly
            100                 105                 110

Gln Asn Ala Val Leu Gln Val Phe Thr Ala Ala Ser Trp Lys Thr Met
            115                 120                 125

Cys Ser Asp Asp Trp Lys Gly His Tyr Ala Asn Val Ala Cys Ala Gln
130                 135                 140

Leu Gly Phe Pro Ser Tyr Val Ser Ser Asp Asn Leu Arg Val Ser Ser
145                 150                 155                 160

Leu Glu Gly Gln Phe Arg Glu Glu Phe Val Ser Ile Asp His Leu Leu
                165                 170                 175

Pro Asp Asp Lys Val Thr Ala Leu His His Ser Val Tyr Val Arg Glu
            180                 185                 190

Gly Cys Ala Ser Gly His Val Val Thr Leu Gln Cys Thr Ala Cys Gly
            195                 200                 205

His Arg Arg Gly Tyr Ser Ser Arg Ile Val Gly Gly Asn Met Ser Leu
        210                 215                 220

Leu Ser Gln Trp Pro Trp Gln Ala Ser Leu Gln Phe Gln Gly Tyr His
225                 230                 235                 240

Leu Cys Gly Gly Ser Val Ile Thr Pro Leu Trp Ile Ile Thr Ala Ala
                245                 250                 255

His Cys Val Tyr Glu Ile Val Ala Pro Arg Glu Arg Ala Asp Arg Arg
            260                 265                 270

Gly Arg Lys Leu Leu Cys Trp Arg Lys Pro Thr Lys Met Lys Gly Pro
        275                 280                 285

Arg Pro Ser His Ser
        290
```

TARGET CA125 PEPTIDES FOR CANCER IMMUNOTHERAPY

This application claims priority under 35 U.S.C. §119(e) from U.S. provisional patent application Ser. No. 60/849,721, filed Oct. 5, 2006.

STATEMENT OF GOVERNMENT SUPPORT

The research that led to this invention was supported by grant DAMD17-03-1-0415 from the United States Department of the Army. The United States government may have rights in this invention.

BACKGROUND OF THE INVENTION

Despite advances in post-surgical chemotherapy for ovarian cancer, nearly 90% of advanced cases will develop progressive disease that is refractory to salvage chemotherapy regimens. In response to the need for alternative treatments that prevent disease recurrence or progression, tumor-specific immunologic intervention has received some attention.

TADG-12 is a serine protease highly expressed in ovarian cancer, but with limited expression in normal human tissues (1). CA125/MUC16 is the best known ovarian tumor-associated antigen and its secreted form has long been recognized as the gold standard for monitoring patients with ovarian carcinoma.

Role of Dendritic Cells in T Cell Immunity

Dendritic cells (DC) are rare but highly potent antigen presenting cells of bone marrow origin that can stimulate both primary and secondary T and B cell responses (19-24). The combination of two cytokines (i.e., GM-CSF and IL-4) has been shown to generate large numbers of myeloid monocyte-derived DC (9-24). However, after 6-8 days of culture in vitro these DC are still immature. Although they may effectively capture antigens, these immature DC lack full T cell-stimulatory activity and are sensitive to the immunosuppressive effects of several immunoregulatory cytokines that can be produced by tumors (25). In contrast, when maturation is induced by appropriate stimuli, such as monocyte-conditioned medium, LPS, or a cocktail of inflammatory cytokines (e.g., TNFα, IL1β, PGE2a) (26), DC demonstrate a reduced ability to phagocytose antigens, but show a significantly higher production of key cytokines (e.g., IL-12), increased resistance to the immunosuppressive effects of IL-10, increased expression of T cell adhesion and costimulatory molecules, and increased expression of chemokine receptors that guide DC migration into lymphoid organs for priming of antigen-specific T cells (24, 25).

DC and Human Tumor Immunotherapy

Monocyte-derived mature DC-based vaccinations have recently been shown to induce the rapid generation of broad T cell immunity in healthy subjects vaccinated with less than $3 \times 10^6$ antigen-pulsed autologous DC (27, 28). In contrast, the administration of immature DC has been reported to result in inhibition of pre-existing effector T cell function (29). These recently published studies represent the first indisputable evidence of the efficacy of DC vaccination as novel and powerful tools for human immunization. However, at this time, the extent to which general conclusions can be drawn from these observations for the active immunization of cancer patients remain only partially established.

In this regard, only a few clinical trials of DC vaccination have been reported in cancer patients. These studies have sometimes documented the induction of an anti-tumor immune responses and therapeutic benefit. In a study of patients with low grade, chemotherapy-resistant non-Hodgkin's lymphoma, four patients were given a series of subcutaneous injections of DC cultured with tumor-derived idiotype protein (30). All four patients developed lymphoproliferative responses to their own idiotype protein. Clinical responses were also seen, with one patient with pericardial and periaortic masses experiencing complete remission (durable for 42 months at the time of publication), and a second patient becoming PCR-negative (using idiotype-specific primers) and remaining in complete remission for 36 months. The remaining two patients showed stabilization of disease.

In children, vaccination of patients with solid tumors with tumor lysate-pulsed DC has been shown to expand tumor specific T cells and mediate cancer regression (35). Indeed, significant regression of multiple metastatic sites were seen in 1 patient. Five patients showed stable disease, including 3 who had minimal residual disease at the time of vaccine therapy and remain free of tumor with 16-30 months follow-up. Only patients who had failed standard therapies and therefore had been heavily pretreated with chemotherapy were considered eligible for this study. Importantly, all pediatric patients were treated in an outpatient setting without any observable toxicity resulting by DC administration.

Treatments to prevent disease recurrence or progeression in ovarian and other cancers are needed.

SUMMARY

Both TADG-12 and CA125 have tightly limited tissue expressions. Their expression is much higher in ovarian cancer tissue than normal ovary. Obtaining sufficient amounts of tumor antigen from a patient for the development of DC-based immunotherapy against the patient's own tumor will be not possible in many cases. It would be preferable to predetermine immunogenic peptides of antigens commonly present on tumors that could be prepared synthetically in quantity for use in immunotherapy.

The invention is based on the discovery of peptides in TADG-12 and CA 125 that can be used to induce an autologous T cell response that lyses ovarian cancer cells expressing TADG-12 or CA125. A computer algorithm was used to select 9-mer and 10-mer peptides from CA125 and TADG-12 that were predicted to bind to the antigen-presenting groove of HLA class I protein A2. HLA A2 is the most common and the most well characterized HLA class I cell surface protein. It is present in approximately 50% of the population. Several 9-mer and 10-mer peptides from both TADG-12 and CA125 predicted to bind to HLA A2 were loaded onto dendritic cells having the HLA A2 antigen, and the peptide-loaded dendritic cells were used to amplify autologous CD8+ T cells ex vivo. Most of the peptides tested amplified CD8+ T cells that recognized and lysed autologous cells pulsed with the peptide. At least one CA125 peptide and at least one TADG-12 peptide consistently produced amplified CD8+ T cells, even from cancer patients, that lysed autologous CA 125-expressing or TADG-12-expressing tumor cells.

Accordingly, one embodiment of the invention provides a method of treating cancer in a patient whose cancer cells express CA125 involving: (a) contacting antigen-presenting cells with a purified peptide comprising an HLA-binding CA125 peptide of 7-12 amino acid residues to generate peptide-loaded antigen-presenting cells; (b) contacting the peptide-loaded antigen-presenting cells with T cells of the cancer patient to amplify CD8+ T cells that recognize the CA125 peptide; and (c) contacting the amplified CD8+ T cells with CA125-bearing cancer cells in the patient to lyse the CA125-bearing cancer cells. The CA125 peptide binds to a human class I HLA protein. When the CA125 peptide is bound to the HLA protein on the surface of antigen-presenting cells to generate peptide-loaded antigen-presenting cells, and the peptide-loaded antigen-presenting cells are contacted with T cells, the peptide-loaded antigen-presenting cells amplify CD8+ T cells that lyse autologous cells expressing CA125 in vivo or in vitro. Preferably the antigen-presenting cells are dendritic cells.

Another embodiment of the invention provides a method of treating cancer in a patient whose cancer cells express TADG-12 involving: (a) contacting antigen-presenting cells with a purified peptide comprising an HLA-binding TADG-12 peptide of 7-12 amino acid residues to generate peptide-loaded antigen-presenting cells; (b) contacting the peptide-loaded antigen-presenting cells with T cells of the cancer patient to amplify CD8+ T cells that recognize the TADG-12 peptide; and (c) contacting the amplified CD8+ T cells with TADG-12-bearing cancer cells in the patient to lyse the TADG-12-bearing cancer cells. The TADG-12 peptide binds to a human class I HLA protein. When the TADG-12 peptide is bound to the HLA protein on the surface of antigen-presenting cells to generate peptide-loaded antigen-presenting cells, and the peptide-loaded dendritic cells are contacted with T cells, the peptide-loaded dendritic cells amplify CD8+ T cells that lyse autologous cells expressing TADG-12 in vivo or in vitro. Preferably, the antigen-presenting cells are dendritic cells.

Another embodiment of the invention provides a purified CA125 peptide of 7-50 amino acid residues, wherein the peptide binds to a human class I HLA protein, wherein when the peptide is bound to the HLA protein on the surface of dendritic cells to generate peptide-loaded dendritic cells, and the peptide-loaded dendritic cells are contacted with T cells, the peptide-loaded dendritic cells amplify CD8+ T cells that lyse autologous cells expressing CA125 in vivo or in vitro.

Another embodiment of the invention provides a purified CA125 peptide of 7-50 amino acid residues, wherein the peptide binds to a human class I HLA protein, wherein when the peptide is bound to the HLA protein on the surface of dendritic cells to generate peptide-loaded dendritic cells, and the peptide-loaded dendritic cells are contacted with T cells, the peptide-loaded dendritic cells amplify CD8+ T cells that lyse in vitro autologous lymphoblastoid cell line (LCL) cells pulsed with the peptide.

Another embodiment of the invention provides a purified TADG-12 peptide of 7-50 amino acid residues, wherein the peptide binds to a human class I HLA protein, wherein when the peptide is bound to the HLA protein on the surface of dendritic cells to generate peptide-loaded dendritic cells, and the peptide-loaded dendritic cells are contacted with T cells, the peptide-loaded dendritic cells amplify CD8+ T cells that lyse autologous cells expressing TADG-12 in vivo or in vitro.

Another embodiment of the invention provides a purified CA125 peptide of 7-50 amino acid residues, wherein the peptide binds to a human class I HLA protein, wherein when the peptide is bound to the HLA protein on the surface of dendritic cells to generate peptide-loaded dendritic cells, and the peptide-loaded dendritic cells are contacted with T cells, the peptide-loaded dendritic cells amplify CD8+ T cells that lyse in vitro autologous lymphoblastoid cell line (LCL) cells pulsed with the peptide.

Another embodiment of the invention provides a pharmaceutical composition comprising: dendritic cells loaded ex vivo with a purified peptide comprising an HLA-binding CA125 peptide of 7 to 12 amino acid residues; wherein the HLA-binding CA125 peptide binds to a human class I HLA protein on the surface of the dendritic cells, and wherein when the CA125 peptide is bound to the HLA protein on the surface of dendritic cells to generate peptide-loaded dendritic cells, and the peptide-loaded dendritic cells are contacted with T cells, the peptide-loaded dendritic cells amplify CD8+ T cells that lyse autologous cells expressing CA125 in vivo or in vitro. Optionally, the dendritic cells could be replaced with other antigen-presenting cells.

Another embodiment of the invention provides a pharmaceutical composition comprising: dendritic cells loaded ex vivo with a purified peptide comprising an HLA-binding TADG12 peptide of 7 to 12 amino acid residues; wherein the TADG12 peptide binds to a human class I HLA protein on the surface of the dendritic cells, and wherein when the TADG 12 peptide is bound to the HLA protein on the surface of dendritic cells to generate peptide-loaded dendritic cells, and the peptide-loaded dendritic cells are contacted with T cells, the peptide-loaded dendritic cells amplify CD8+ T cells that lyse autologous cells expressing TADG12 in vivo or in vitro. Optionally, the dendritic cells could be replaced with other antigen-presenting cells.

Another embodiment of the invention provides a pharmaceutical composition comprising: amplified CD8+ T cells that lyse autologous cells expressing CA125 in vivo or in vitro. The amplified CD8+ T cells are amplified by a process comprising: contacting T cells ex vivo with dendritic cells loaded ex vivo with a CA125 peptide of 7 to 12 amino acid residues; wherein the peptide binds to a human class I HLA protein on the surface of the dendritic cells. The peptide is bound to the HLA protein on the surface of dendritic cells to generate peptide-loaded dendritic cells, and the peptide-loaded dendritic cells are contacted with T cells, the peptide-loaded dendritic cells amplify CD8+ T cells that lyse autologous cells expressing CA125 in vivo or in vitro. The T cells and dendritic cells share the same HLA class I protein. Optionally, the dendritic cells could be replaced with other antigen-presenting cells.

Another embodiment of the invention provides a pharmaceutical composition comprising: amplified CD8+ T cells that lyse autologous cells expressing TADG-12 in vivo or in vitro. The amplified CD8+ T cells are amplified by a process comprising: contacting T cells ex vivo with dendritic cells loaded ex vivo with a TADG-12 peptide of 7 to 12 amino acid residues; wherein the peptide binds to a human class I HLA protein on the surface of the dendritic cells. The peptide is bound to the HLA protein on the surface of dendritic cells to generate peptide-loaded dendritic cells, and the peptide-loaded dendritic cells are contacted with T cells, the peptide-loaded dendritic cells amplify CD8+ T cells that lyse autologous cells expressing TADG-12 in vivo or in vitro. The T cells and dendritic cells share the same HLA class I protein. Optionally, the dendritic cells could be replaced with other antigen-presenting cells.

Another embodiment of the invention provides a method of identifying a CA125 peptide suitable for cancer immunotherapy comprising: (a) contacting one or more candidate peptides comprising an HLA-binding CA125 peptide of 7 to 12 amino acid residues with dendritic cells expressing an HLA class I protein to generate peptide-loaded dendritic cells; (b) contacting the peptide-loaded dendritic cells with HLA class I-matched T cells to generate amplified T cells that recognize the CA125 peptide; and (c) contacting the amplified T cells with target cells expressing CA125 to determine whether the amplified T cells lyse the target cells. Optionally, the dendritic cells could be replaced with other antigen-presenting cells.

Another embodiment of the invention provides a method of identifying a TADG12 peptide suitable for cancer immunotherapy comprising: (a) contacting one or more candidate peptides comprising an HLA-binding TADG12 peptide of 7 to 12 amino acid residues with dendritic cells expressing an HLA class I protein to generate peptide-loaded dendritic cells; (b) contacting the peptide-loaded dendritic cells with HLA class I-matched T cells to generate amplified T cells that recognize the TADG12 peptide; and (c) contacting the amplified T cells with target cells expressing TADG12 to determine whether the amplified T cells lyse the target cells. Optionally, the dendritic cells could be replaced with other antigen-presenting cells.

DETAILED DESCRIPTION

Definitions

Figure 1:
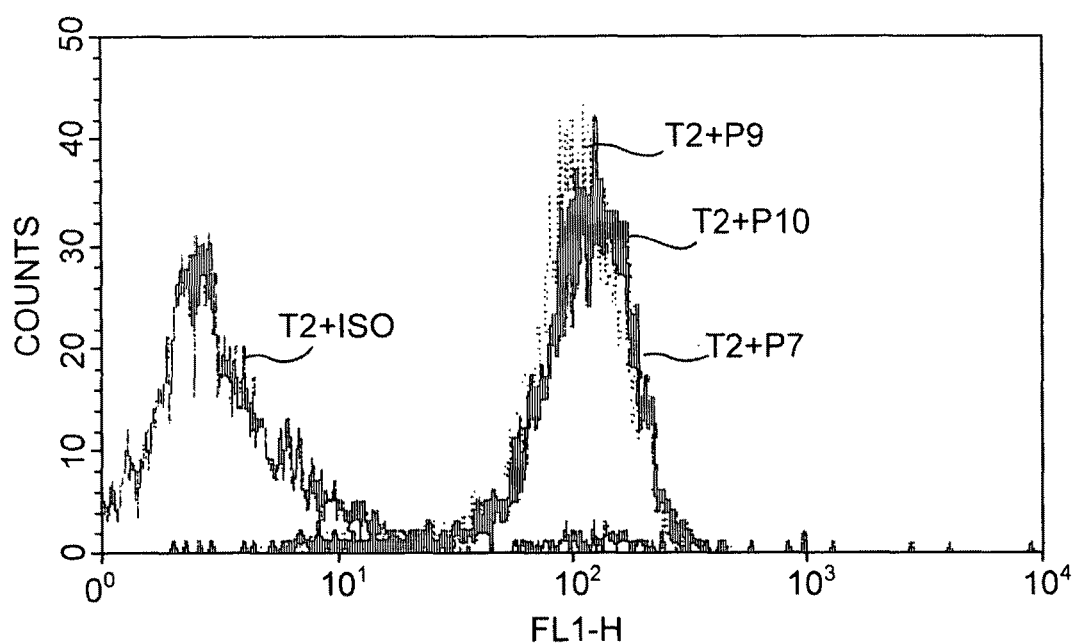
FIG. 1. T2 binding assay for peptide association with HLA A*0201 for 3 representative CA125-derived peptides (P7, P9, and P10). T2 cells were incubated overnight at 37° C. with 50 μg/ml peptide, and cell surface expression of HLA A*0201 was assessed by flow cytometric staining with BB7.2 MAb specific for HLA A*0201. The melanoma antigen gp100 209-217 peptide was used as a positive control (data not shown).

The term "peptide" as used herein includes polypeptides of from about 6 to about 5000 amino acid residues in length.

The term "peptide-loaded dendritic cell" as used herein refers to a dendritic cell presenting a peptide on its surface in a manner effective to amplify CD8+ T cells that specifically recognize the peptide. The dendritic cell may become loaded with the peptide by directly binding the peptide from the medium on its surface, or by processing the peptide intracytoplasmically before presenting the peptide. Processing the peptide may include proteolytically generating the presented peptide from a longer peptide. CD8+ T cells that specifically recognize the peptide are CD8+ T cells that kill autologous cells pulsed with the peptide, as described in Examples 7 and 8 below. For instance, a dendritic cell contacted with a 50-amino-acid-residue peptide that contains a 10-mer CA125 peptide, is considered loaded with the 10-mer CA125 peptide if the CD8+ T cells it amplifies are able to lyse autologous lymphoblastoid cell lines pulsed with just the 10-mer CA125 peptide.

The terms "HLA-binding CA125 peptide of 7-12 amino acid residues" and "HLA-binding TADG12 peptide of 7-12 amino acid residues" refer to peptides of 7-12 amino acids in length whose sequences are found in CA125 or TADG-12, respectively, that bind to an HLA class I cell surface protein. Binding to an HLA class I cell surface protein can be predicted by computer algorithm as described herein in Examples 1 and 2 or experimentally determined as described herein in Examples 5 and 6. The terms "HLA-binding CA125 peptide of 7-12 amino acid residues" and "HLA-binding TADG12 peptide of 7-12 amino acid residues" also refer to peptides of 7-12 residues where up to 3 residues are altered from the native residues found in CA125 or TADG12 without substantial deleterious effect on the ability of the peptide to bind to the HLA class I molecule or the ability of the peptide to be used to amplify CD8+ T cells that kill tumor cells expressing CA125 or TADG-12.

The terms "HLA class I-matched" and "sharing the same HLA class I protein" are synonymous and mean that the two cells or cell types have at least one HLA class I protein in common, such as HLA A*0201.

The term "contacting dendritic cells (or antigen-presenting cells) with a purified peptide" includes any means of contacting, including, e.g., mixing the purified peptide and the cells in medium, mixing the purified peptide in liposomes with the cells, or expressing the purified peptide from a recombinant nucleic acid in the cells.

The term "TADG-12" as used herein includes the TADG-12V isoform.

Description:

Dendritic cells are effective antigen-presenting cells. They are particularly adept at stimulating naive T cells. Dendritic cell function is reviewed in references 25 and 31. The invention involves stimulating CD8+ T cells, also known as cytotoxic T lymphocytes (CTL) that recognize particular peptides derived from the tumor antigens CA125 and TADG-12. That stimulation is preferably done with dendritic cells. It may be possible to do it with other antigen-presenting cells or by some other method developed in the future.

One embodiment of the invention provides a method of treating cancer in a patient whose cancer cells express CA125 involving: (a) contacting dendritic cells with a purified peptide comprising an HLA-binding CA125 peptide of 7-12 amino acid residues to generate peptide-loaded dendritic cells; (b) contacting the peptide-loaded dendritic cells with T cells of the cancer patient to amplify CD8+ T cells that recognize the CA125 peptide; and (c) contacting the amplified CD8+ T cells with CA125-bearing cancer cells in the patient to lyse the CA125-bearing cancer cells. The CA125 peptide binds to a human class I HLA protein.

The step of contacting dendritic cells with a purified peptide is preferably done ex vivo. It may be possible alternatively to perform the step in vivo in the patient.

The step of contacting dendritic cells with a purified peptide may be done by any suitable method, including mixing the dendritic cells with the purified peptide directly, mixing dendritic cells with purified peptide in liposomes, and expressing the purified peptide from a recombinant nucleic acid in the dendritic cells.

In one embodiment, step (a) is performed ex vivo, step (b) involves infusing the peptide-loaded dendritic cells into the patient to amplify the CD8+ T cell in vivo in the patient, and step (c) occurs in vivo in the patient.

In another embodiment, steps (a) and (b) are performed ex vivo, and step (c) involves infusing the amplified CD8+ T cells into the patient to contact the CA125-bearing cancer cells in vivo in the patient.

The purified peptide contacted with the dendritic cells may be a peptide of any appropriate length, e.g., 7 to 5000 amino acid residues. CA125 has a long N-terminal domain, a multiple repeat domain, and a transmembrane C-terminal domain (2, 32). Suitable peptide antigens may be found in any domain. The peptides tested herein are from the multiple repeat domain, which extends from residue 12070 to residues 21868 of the CA125 sequence in reference 32 (GenBank accession number AAL65133). The multiple repeat domain consists of 156-amino-acid repeat units that are homolgous to each other. The individual repeat units are homologous to each other. In some embodiments, the HLA-binding CA125 peptide of 7-12 amino acid residues is from the multiple repeat domain.

In a preferred embodiment, the purified peptide contacted with dendritic cells is a short peptide that does not need to be proteolytically processed to be presented by the dendritic cells. In particular embodiments, the purified peptide is 7-50, 7-30, 7-20, 7-12, or 8-10 amino acid residues in length. The purified peptide may comprise only CA125 sequence or may comprise other sequences. It may be a naturally-derived fragment of CA 125. Alternatively, it may be, for instance, a long peptide comprising a multiple repeat of a single CA125 8- to 10-mer peptide sequence.

The CA125 peptide used in the invention binds to a human class I HLA protein. There are several variants of HLA class I protein, including HLA A*0201. Other variants include HLA A1, A24, B14, and CwO301. The affinity of particular 8-10 mer peptides for one of these or other HLA class I cell surface proteins can be calculated with an algorithm on the NIH website bimas.dcrt.nih.gov/molbio/hla_bind. The algorithm is described in reference (3). Candidate peptides for screening can be identified by screening the CA125 protein sequence (GenBank accession number AAL65133 and disclosed in reference 32) for 8- to 10-mer peptide sequences with affinity for HLA class I proteins with the BIMAS program.

Whether a peptide binds to an HLA class I protein can be determined experimentally as described in Examples 3 and 4 below.

When the CA125 peptide is bound to the HLA class I protein on the surface of dendritic cells to generate peptide-loaded dendritic cells, and the peptide-loaded dendritic cells are contacted with T cells, the peptide-loaded dendritic cells amplify CD8+ T cells that lyse autologous cells expressing CA125 in vivo or in vitro. Dendritic cells can be loaded with the peptides and used to amplify CD8+ T cells as described in Examples 5 and 6 below. The ability of the amplified CD8+ T cells to lyse autologous cells expressing CA125 can be tested as described in Examples 9 and 10 below. Preferably the autologous cells are cancer cells expressing CA125.

The amplified T cells can also be tested for the ability to lyse autologous cells pulsed with the CA 125 peptide of 7-12 amino acid residues as described in Examples 7 and 8 below.

In the assay and in the method of treating cancer, the T cells are ordinarily autologous with the cancer cells or other cells expressing CA125. Preferably, the dendritic cells are also autologous to the T cells and the cells expressing CA125. However allogeneic dendritic cells sharing at least one HLA class I cell surface protein may also be used.

To treat a patient for cancer, dendritic cells may be prepared in vitro and loaded with the appropriate peptide. The peptide-loaded dendritic cells may then be infused into a patient. They will then amplify T cells in the patient that recognize the peptide and recognize and lyse cancer cells expressing CA125.

The dendritic cells may be infused intravenously into the patient as described in Example 12 below. They may also be administered by another route, such as subcutaneously. Preferably dendritic cells are administered multiple times to a patient, e.g., three times with two weeks between treatments.

As an alternative to administering peptide-loaded dendritic cells to the patient, the peptide-loaded dendritic cells can be used to amplify CD8+ T cells from the patient ex vivo, as described in Examples 5 and 6 below. The amplified T cells may be then infused into the patient. As many amplified T cells as can be obtained would typically be infused.

The dendritic cells to amplify T cells ex vivo, or for infusion into the patient, may be allogeneic or autologous. Whether allogeneic or autologous, they will have a short life span in the body, so they are not expected to induce a hazardous autoimmune response. The CD8+ T cells, if prepared ex vivo, are preferably autologous, but may be allogeneic. If they are allogeneic, they may produce a graft-versus-host disease.

In the method of treating cancer, the CA125-bearing cancer cells may be any type of cancer expressing CA125. Ovarian carcinoma is best known for expressing CA125, but other cancer types are also known to often express CA125, including lymphoma, and specifically non-hodgkin's lymphoma.

The preferred HLA-binding CA125 peptide of 7-12 amino acids is YTLDRDSLYV (SEQ ID NO: 10). This peptide is shown below to amplify CD8+ T cells that consistently lyse autologous ovarian tumor cells expressing CA125. Several other CA125 peptides were shown to bind to HLA A*0201, to amplify CD8+ T cells that lyse autologous cells pulsed with the peptide. And some of these appeared to lyse tumor cells expressing CA 125 at least inconsistently, but only SEQ ID NO: 10 was found to amplify T cells that lysed the tumor cells consistently. Given that one CA125 peptide can amplify CD8+ T cells that lyse tumor cells, others could be identified with further screening.

In particular embodiments, the CA125 peptide comprises SEQ ID NO:10. In other embodiments, it comprises at least 7 amino acid residues of SEQ ID NO: 10 in the same order and with the spacing as in SEQ ID NO: 10 (i.e., where 3 of the 10 residues of SEQ ID NO: 10 are replaced with other residues or are absent on the ends of the peptide). In other embodiments, it comprises at least 8, or at least 9 amino acid residues of SEQ ID NO: 10 in the same order and with the spacing as in SEQ ID NO: 10. In particular embodiments, the peptide comprises at least 7, 8, or 9 contiguous residues of SEQ ID NO: 10.

In the detailed description above, the term "CA125" can be replaced with "TADG-12" to describe the analogous method of treating cancer in a patient whose cancer cells express TADG-12.

The affinity of particular 8-10-mer peptides of TADG-12 and TADG-12V for HLA class I cell surface proteins can be calculated with the BIMAS algorithm on the NIH website bimas.dcrt.nih.gov/molbio/hla_bind. The algorithm is described in reference (3). Candidate peptides for screening can be identified by screening the TADG-12 and TADG-12V protein sequences (SEQ ID NO:21 and 22, Tables 1 and 2) for 8-10-mer peptide sequences with affinity for HLA class I proteins using the BIMAS algorithm on the NIH website bimas.dcrt.nih.gov/molbio/hla_bind. TADG-12 and TADG-12V are identical through the first 256 amino acid residues.

TABLE 1

TADG-12 protein sequence.

(SEQ ID NO: 21)

```
  1 MGENDPPAVE APFSFRSLFG LDDLKISPVA PDADAVAAQI LSLLPLKFFP

51 IIVIGIIALI LALAIGLGIH FDCSGKYRCR SSFKCIELIA RCDGVSDCKD

101 GEDEYRCVRV GGQNAVLQVF TAASWKTMCS DDWKGHYANV ACAQLGFPSY

151 VSSDNLRVSS LEGQFREEFV SIDHLLPDDK VTALHHSVYV REGCASGHVV

201 TLQCTACGHR RGYSSRIVGG NMSLLSQWPW QASLQFQGYH LCGGSVITPL

251 WIITAAHCVY DLYLPKSWTI QVGLVSLLDN PAPSHLVEKI VYHSKYKPKR

301 LGNDIALMKL AGPLTFNEMI QPVCLPNSEE NFPDGKVCWT SGWGATEDGA

351 GDASPVLNHA AVPLISNKIC NHRDVYGGII SPSMLCAGYL TGGVDSCQGD

401 SGGPLVCQER RLWKLVGATS FGIGCAEVNK PGVYTRVTSF LDWIHEQMER

451 DLKT
```

TABLE 2

TADG-12V protein sequence.

(SEQ ID NO: 22)
```
  1 MGENDPPAVE APFSFRSLFG LDDLKISPVA PDADAVAAQI LSLLPLKFFP

51 IIVIGIIALI LALAIGLGIH FDCSGKYRCR SSFKCIELIA RCDGVSDCKD

101 GEDEYRCVRV GGQNAVLQVF TAASWKTMCS DDWKGHYANV ACAQLGFPSY

151 VSSDNLRVSS LEGQFREEFV SIDHLLPDDK VTALHHSVYV REGCASGHVV

201 TLQCTACGHR RGYSSRIVGG NMSLLSQWPW QASLQFQGYH LCGGSVITPL

251 WIITAAHCVY EIVAPRERAD RRGRKLLCWR KPTKMKGPRP SHS
```

For use in the method of treating cancer in a patient whose cancer cells express TADG-12, the preferred TADG-12 peptide is YLPKSWTIQV (SEQ ID NO: 17). This peptide is shown below to amplify CD8+ T cells that consistently lyse autologous ovarian tumor cells expressing TADG-12. Several other TADG-12 peptides were shown to bind to HLA A*0201, to amplify CD8+ T cells that lyse autologous cells pulsed with the peptide. And some of these appeared to lyse tumor cells expressing TADG-12 at least inconsistently, but only SEQ ID NO: 17 was found to amplify T cells that lysed the tumor cells consistently. Given that one TADG-12 peptide can amplify CD8+ T cells that lyse tumor cells, others most likely could be identified with further screening.

In particular embodiments, the TADG-12 peptide comprises SEQ ID NO:17. In other embodiments, it comprises at least 7 amino acid residues of SEQ ID NO: 17 in the same order and with the spacing as in SEQ ID NO: 17 (i.e., where 3 of the 10 residues of SEQ ID NO: 17 are replaced with other residues or are absent on the ends of the peptide). In other embodiments, it comprises at least 8, or at least 9 amino acid residues of SEQ ID NO: 17 in the same order and with the spacing as in SEQ ID NO: 17. In particular embodiments, the peptide comprises at least 7, 8, or 9 contiguous residues of SEQ ID NO:17.

The invention will now be illustrated with the following non-limiting examples.

EXAMPLES

Example 1

Selection of CA125 Peptides

The multiple repeat domain of the CA125 sequence, residues 12070 to 21868 of CA125 (GenBank Accession Number AAL65133) was processed using the BIMAS algorithm of the Center for Information Technology, NIH, (web address: bimas.dcrt.nih.gov/molbio/hla_bind) to identify candidate peptides predicted to bind to the most abundant HLA class I cell surface protein (3). The website allows calculation of binding affinity to different HLA proteins. Since HLA A*0201 is represented in approximately half the population, binding was calculated to that HLA molecule. Twelve CA125 9-mer or 10-mer peptides with strong predicted binding to HLA A*0201 were selected for further testing (Table 3). In Tables 3 and 4, one amino acid in the peptide sequence is lower case. For peptides longer than 9 amino acids, the algorithm to calculate binding affinity postulates that one amino acid in the middle of the peptide bulges out, and this amino acid is not used to calculate affinity. It is this amino acid that is in lower case.

TABLE 3

| Peptide ID | CA125 PEPTIDES HLA A-0201 | No. of AA | BIMAS SCORE |
|---|---|---|---|
| P1 CA125/9 | WLGSTYQLV (SEQ ID NO: 1) | 9 | 479.909 |
| P2 CA125/9 | VLFTLNFTI (SEQ ID NO: 2) | 9 | 380.609 |
| P3 CA125/9 | LLDRGSLYV (SEQ ID NO: 3) | 9 | 260.124 |
| P4 CA125/9 | YLGCQLISL (SEQ ID NO: 4) | 9 | 226.014 |
| P5 CA125/9 | TLNASFHWL (SEQ ID NO: 5) | 9 | 223.237 |
| P6 CA125/9 | GVTQLGFYV (SEQ ID NO: 6) | 9 | 194.137 |
| P7 CA125/10 | YLLDrGSLYV (SEQ ID NO: 7) | 10 | 26694.1 |
| P8 CA125/10 | QLHDtFRFCL (SEQ ID NO: 8) | 10 | 1930.39 |
| P9 CA125/10 | LLMPfTLNFT (SEQ ID NO: 9) | 10 | 592.944 |
| P10 CA125/10 | YTLDrDSLYV (SEQ ID NO: 10) | 10 | 370.752 |
| P11 CA125/10 | FMVPfTLNFT (SEQ ID NO: 11) | 10 | 313.179 |
| P12 CA125/10 | TLLVtGTSRV (SEQ ID NO: 12) | 10 | 257.342 |

Example 2

Selection of TADG-12 Peptides

The TADG-12 (Tumor Associated Differentially Expressed Gene 12) protein sequence (SEQ ID NO:21) (1) was processed using the BIMAS algorithm of the Center for Information Technology, NIH, (web address: bimas.dcrt.nih.gov/molbio/hla_bind) to identify candidate peptides predicted to bind to the most abundant HLA class I cell surface protein (3). The website allows calculation of binding affinity to different HLA proteins. Since HLA A*0201 is represented in approximately half the population, binding was calculated to that HLA molecule. Eight TADG-12 9-mer and 10-mer peptides with strong predicted binding to HLA A*0201 were selected for further testing (Table 4).

TABLE 4

| Peptide ID | TADG-12 PEPTIDES HLA A-0201 | No. of AA | BIMAS SCORE |
|---|---|---|---|
| P1 TADG12/9 | AQLGFPSYV (SEQ ID NO: 13) | 9 | 545.316 |
| P2 TADG12/9 | LLPLKFFPI (SEQ ID NO: 14) | 9 | 195.448 |
| P3 TADG12/10 | SLLPIKFFPI (SEQ ID NO: 15) | 10 | 425.387 |
| P4 TADG12/10 | LLPDdKVTAL (SEQ ID NO: 16) | 10 | 342.461 |
| P5 TADG12/10 | YLPKsWTIQV (SEQ ID NO: 17) | 10 | 319.939 |
| P6 TADG12/10 | GLDDIKISPV (SEQ ID NO: 18) | 10 | 262.35 |
| P7 TADG12/10 | KLVGaTSFGI (SEQ ID NO: 19) | 10 | 211.786 |
| P8 TADG12/10 | SLLSqWPWQA (SEQ ID NO: 20) | 10 | 137.862 |

Example 3

CA 125 Peptide Binding to HLA A*0201 on T2 Cells

Peptide binding assays were conducted with the TAP-deficient T2 cell line using the 12 CA 125 peptides of Table 3. Ten out of the 12 CA125 peptides predicted to have a long half life of binding to HLA A*0201 by the BIMAS computer algorithm significantly increased cell expression of A*0201, as determined by flow cytometric analysis. The results with three representative peptides are shown in FIG. 1.

Example 4

TADG-12 Peptide Binding to HLA A*0201 on T2 Cells

Figure 2:
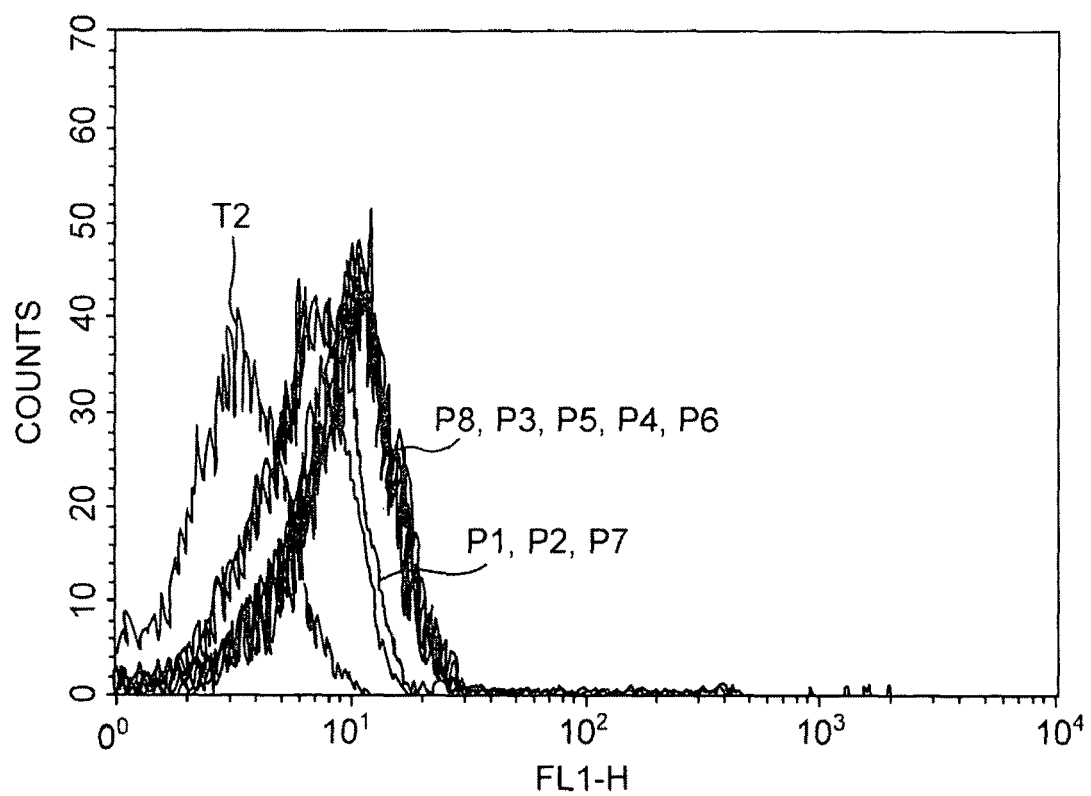
FIG. 2. T2 binding assay for peptide association with HLA A*0201 for all 8 TADG12-derived peptides. T2 cells were incubated overnight at 37° C. with 50 μg/ml peptide, and cell surface expression of HLA A*0201 was assessed by flow cytometric staining with BB7.2 MAb specific for HLA A*0201.

Peptide binding assays were conducted with the TAP-deficient T2 cell line using the 8 TADG-12 peptides of Table 4. Six out of the 8 TADG-12 peptides predicted to have a long half life of binding to HLA A*0201 by the BIMAS computer algorithm significantly increased cell expression of A*0201, as determined by flow cytometric analysis. The results with all of the TADG-12 peptides are shown in FIG. 2.

Example 5

Figure 3:
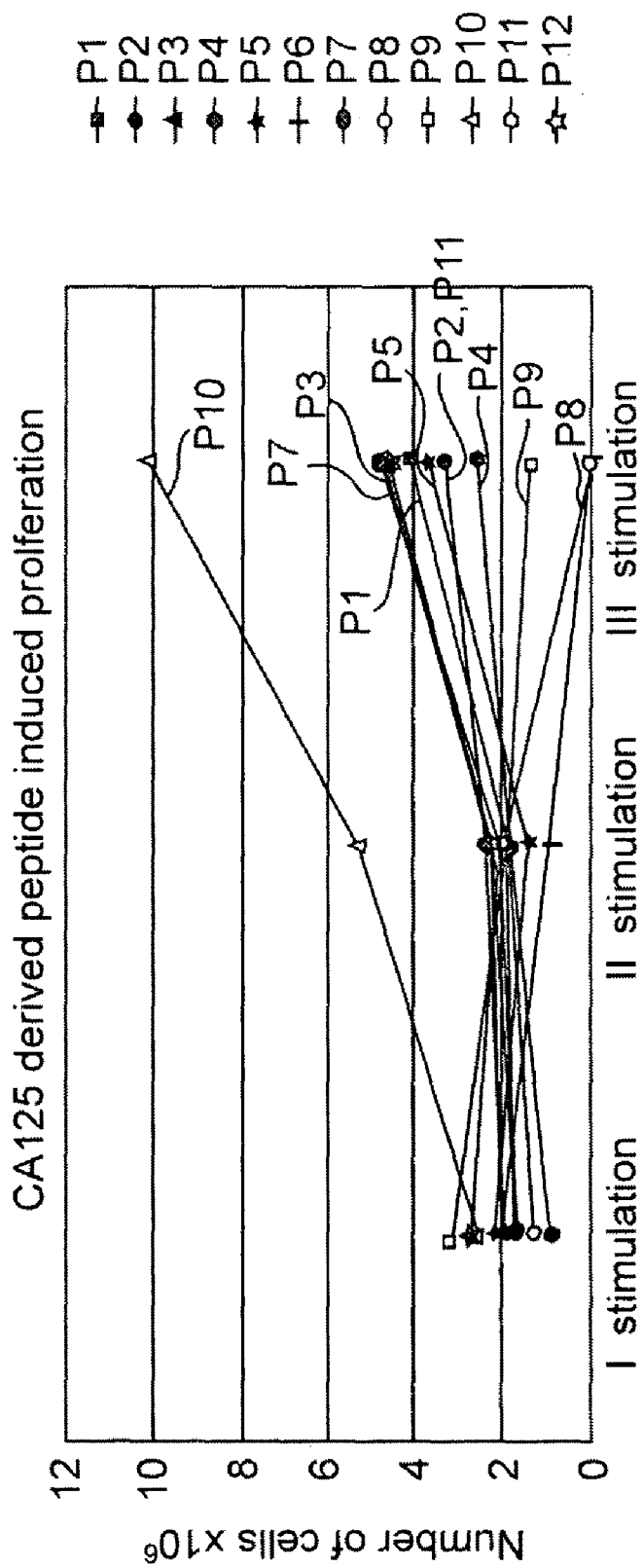
FIG. 3. Proliferative responses by autologous dendritic cells pulsed with 12 CA125-derived peptides. CD8+ T cell numbers up to the time of the third stimulation are shown.

Dendritic Cell-Induced CD8+Proliferative Responses Against CA125 Peptides in Healthy Donors Cryopreserved peripheral blood leukocytes (PBL) from healthy HLA-A2 positive donors were used for generation of dendritic cells (DC). Monocyte-derived DC were cultured in AIM-V (Gibco-BRL) supplemented with GM-CSF and IL-4 (4). After 5 days' culture, DC maturation was induced by addition of TNFα, IL-1, and $GPE_2$ (4). Mature DC were pulsed for 1-2 hours at 37° C. with 50 μg/ml of the selected CA125 peptide of Table 3, and washed twice before culture with PBL at a responder:stimulator ratio of 30:1. The culture medium was AIM-V plus 5% human AB serum (Gemini Bioproducts). No IL-2 was added. After 7 days, responder T cells were collected and restimulated with peptide-pulsed DC. For the second and third DC stimulations, the medium was supplemented with 50-100 U/ml IL-2, and the culture period extended to 14 days. After the third cycle, CD8+ T cells were recovered by positive selection with anti-CD8 magnetic beads (Dynal, A. S.). Subsequent restimulations (passages) of CD8+ T cells used peptide-loaded autologous PBL as antigen-presenting cells. Proliferative responses at the time of each restimulation with peptide-loaded autologous DC targets were seen against the majority of CA125 peptides (FIG. 3). The highest proliferative response was with peptide 10 (YTLDRDSLYV, SEQ ID NO: 10) (FIG. 3).

Example 6

Figure 4:
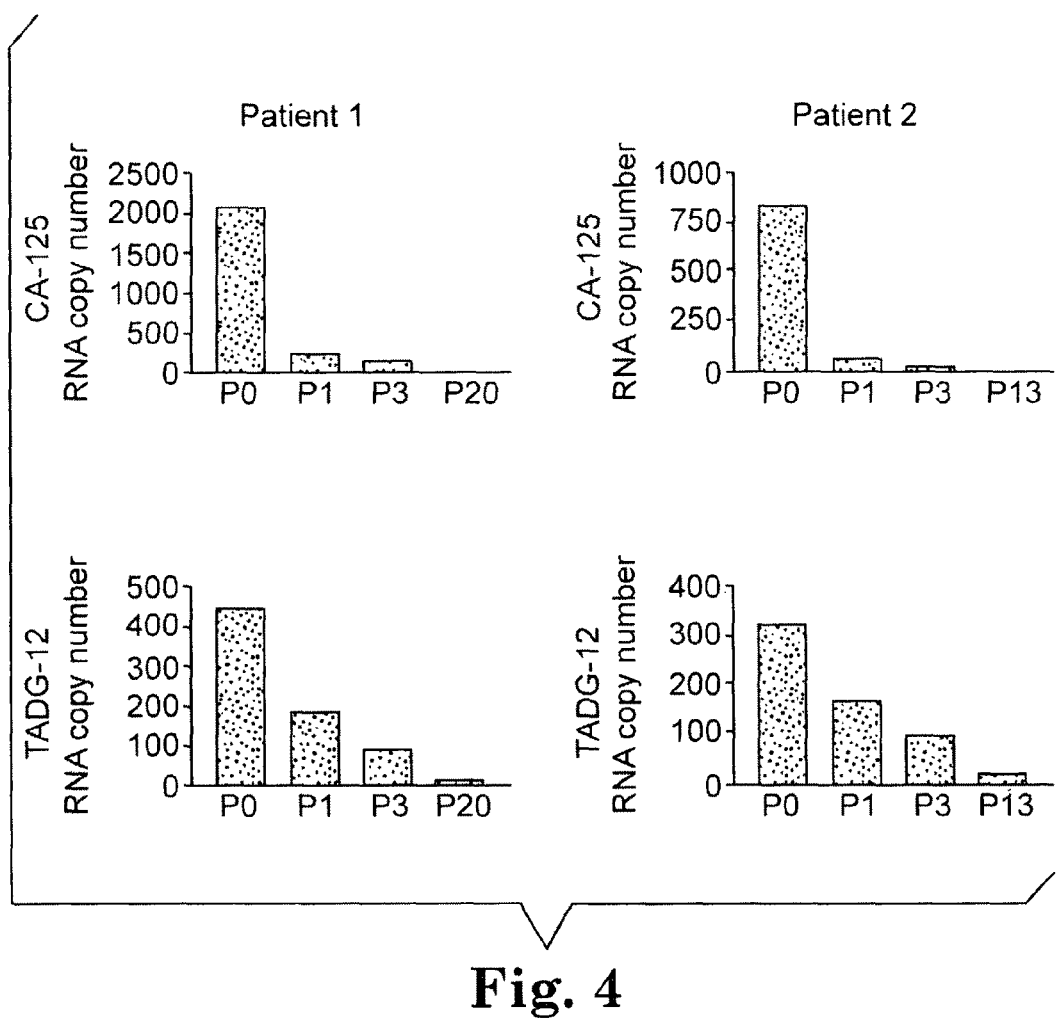
FIG. 4. q-RT-PCR analysis of CA125 and TADG-12 expression in Patient 1 and 2. The Y axis represents the fold induction relative to normal ovary expression. The X axis represents each sample from patient 1 and 2 tested for CA125 and TADG-12 expression at different time points of in vitro culture (i.e., tumors never passed in culture to a new flask=P0, and tumors passed once=P1).

Dendritic Cell-Induced CD8+ Proliferative Responses Against TADG-12 Peptides in Healthy Donors Cryopreserved peripheral blood leukocytes (PBL) from healthy HLA-A2-positive donors were used for generation of dendritic cells (DC). Monocyte-derived DC were cultured in AIM-V (Gibco-BRL) supplemented with GM-CSF and IL-4 (4). After 5 days' culture, DC maturation was induced by addition of TNFα, IL-1β, and $GPE_2$ (4). Mature DC were pulsed for 1-2 hours at 37° C. with 50 μg/ml of the selected TADG-12 peptide of Table 4, and washed twice before culture with PBL at a responder:stimulator ratio of 30:1. The culture medium was AIM-V plus 5% human AB serum (Gemini Bioproducts). No IL-2 was added. After 7 days, responder T cells were collected and restimulated with peptide-pulsed DC. For the second and third DC stimulations, the medium was supplemented with 50-100 U/ml IL-2, and the culture period extended to 14 days. After the third cycle, CD8+ T cells were recovered by positive selection with anti-CD8 magnetic beads (Dynal, A. S.). Subsequent restimulations (passages) of CD8+ T cells used peptide-loaded autologous PBL as antigen-presenting cells. Proliferative responses at the time of each restimulation with peptide-loaded autologous DC targets were seen against four out of eight TADG-12 peptides (FIG. 4). The highest proliferative response was with P1, P2, P4, and P5 of Table 4.

Example 7

DC-Induced CD8+ T Cell Response Against Cells Pulsed with CA125 Peptides

Dendritic cells were loaded with the CA125 peptides of Table 3 and used to amplify CD8+ T cells cytotoxic against cells displaying the cognate peptide as described in Example 5. The amplified CD8+ T cell lines were tested for cytotoxicity against autologous lymphoblastoid cell lines (LCL) pulsed with the CA125 peptide used to amplify the T cells. Cytotoxicity was tested in a 5 hour $^{51}$Cr-release assay against autologous LCL and autologous LCL pulsed with 50 μg/ml peptide (5, 6). Results are shown in Table 5. Cytotoxic responses against autologous LCL pulsed with the peptide were seen in 4 out of 12 CA125 peptides. Cytotoxicity was inhibited by blocking monoclonal antibody against non-polymorphic HLA A, B, and C determinants (data not shown). Natural killer (NK)-sensitive K562 cells were not lysed (data not shown).

TABLE 5

Cytotoxicity by peptide-specific CD8+ T cells from a healthy donor against autologous LCL pulsed with CA125-derived peptides

| Peptide | % Lysis |
|---|---|
| Peptide 1 | 0 |
| Peptide 2 | 0 |
| Peptide 3 | 0 |
| Peptide 4 | 0 |
| Peptide 5 | 0 |
| Peptide 6 | 0 |
| Peptide 7 | 5 |
| Peptide 8 | 0 |
| Peptide 9 | 0 |
| Peptide 10 | 38 |
| Peptide 11 | 3 |
| Peptide 12 | 5 |

Example 8

DC-Induced CD8+ T Cell Response Against Cells Pulsed with TADG-12 Peptides

Dendritic cells were loaded with the TADG-12 peptides of Table 4 and used to amplify CD8+ T cells cytotoxic against cells displaying the cognate peptide as described in Example 6. The amplified CD8+ T cell lines were tested for cytotoxicity against autologous lymphoblastoid cell lines (LCL) pulsed with the TADG-12 peptide used to amplify the T cells. Cytotoxicity was tested in a 5 hour $^{51}$Cr-release assay against autologous LCL and autologous LCL pulsed with 50 µg/ml peptide (5, 6). Results are shown in Table 6. Cytotoxic responses against autologous LCL pulsed with the peptide were seen in 6 out of 8 TADG-12 peptides. Cytotoxicity was inhibited by blocking monoclonal antibody against non-polymorphic HLA A, B, and C determinants (data not shown). Natural killer (NK)-sensitive K562 cells were not lysed (data not shown).

TABLE 6

Cytotoxicity by peptide-specific CD8+ T cells from a healthy donor against autologous LCL pulsed with TADG-12-derived peptides

| Peptide | % Lysis |
|---|---|
| Peptide 1 | 0 |
| Peptide 2 | 78 |
| Peptide 3 | 61 |
| Peptide 4 | 2 |
| Peptide 5 | 51 |
| Peptide 6 | 0 |
| Peptide 7 | 10 |
| Peptide 8 | 44 |

The results of another assay with T cells amplified from an ovarian cancer patient are shown in Table 7.

TABLE 7

Cytotoxicity by peptide-specific CD8+ T cells from ovarian cancer patient 1 against autologous LCL pulsed with TADG-12-derived peptides

| Peptide | % Lysis |
|---|---|
| Peptide 1 | 10 |
| Peptide 2 | 5 |
| Peptide 3 | 38 |
| Peptide 4 | 9 |
| Peptide 5 | 20 |

TABLE 7-continued

Cytotoxicity by peptide-specific CD8+ T cells from ovarian cancer patient 1 against autologous LCL pulsed with TADG-12-derived peptides

| Peptide | % Lysis |
|---|---|
| Peptide 6 | 10 |
| Peptide 7 | 4 |
| Peptide 8 | 4 |

Example 9

Cytotoxicity of CA125-Derived-Peptide-Specific CD8+ T Cells Against Autologous Ovarian Cancer Cells Expressing CA125

Part 1—Harvesting Cell Samples from Ovarian Cancer Patients and Testing Tumor Samples for CA125 and TADG-12 Expression.

Tumor samples were harvested at the time of surgery and the peripheral blood leukocytes were collected from ovarian cancer patients.

Multiple ovarian cancer biopsies obtained from patients harboring advanced stage ovarian serous papillary carcinoma were obtained at the time of surgery through the Division of Gynecologic Oncology and the Pathology Department at the University of Arkansas for Medical Sciences (UAMS), Little Rock, Ark., under approval of the UAMS Institutional Review Boards and the Army Surgeon General's Human Subjects Research Review Board (HSRRB). Three HLA-A2-positive primary ovarian cancer cell lines found to overexpress CA125 and/or TADG-12 tumor antigens have been established so far after sterile processing of the samples (Table 8). Briefly, viable tumor tissue was mechanically minced in RPMI 1640 to portions no larger than 1-3 mm$^3$ and washed twice with RPMI 1640. The portions of minced tumor were then placed into 250 ml flasks containing 30 ml of enzyme solution [0.14% collagenase Type 1 and 0.01% DNAse 2000 KU/mg; (Sigma)] in RPMI 1640, and incubated on a magnetic stirring apparatus overnight at 4° C. Enzymatically dissociated tumor was then filtered through 150 µm nylon mesh to generate a single cell suspension. The resultant cell suspension was then washed twice in RPMI 1640 plus 10% FBS (fetal bovine serum). Purity of fresh tumor cultures was tested by morphology, immunochemistry staining and/or flow cytometry with antibodies against cytokeratins. Only cell lines containing more than 99% tumor cells were evaluated in cytotoxicity assays. The cell lines were subsequently cultured in RPMI 1640 plus 10% FBS.

TABLE 8

Histology, antigen expression and HLA class I haplotypes of the primary ovarian cancer cell lines so far established in our laboratory:

| Patient | CA125 | TADG12 | Histology | HLA class I |
|---|---|---|---|---|
| 1 | + | + | Serous | A2, B35, B51, Cw4, Cw14 |
| 2 | + | + | Serous | A2, A24, B35, B44, Cw2, Cw6 |
| 3 | + | + | Serous | A2, A24, B7, B49, Cw7 |

Importantly, because tissue digestion and prolonged in vitro cell culture may potentially alter CA125 and TADG-12 antigen expression, primary ovarian cancer cell lines were evaluated before and after several in vitro passages for CA125 and TADG-12 expression by real time PCR and flow cytometry. Briefly, RNA extraction was performed on autologous primary ovarian cancer cell lines when tumor cells were 50% to 80% confluent after no passages (i.e., P0) and up to a maximum of twenty passages in vitro. RNA isolation was performed using TRIzol Reagent (Invitrogen) according to the manufacturer's instructions. To verify integrity, 4 µg of RNA from each sample was run in 1% agarose gel using 18S+28S Ribosomal RNA (Sigma) as positive control. Briefly, five µg of total RNA from each sample was reverse-transcribed using SuperScript III first strand cDNA synthesis (Invitrogen). Ten µl of reverse transcribed RNA samples (from 500 µl of total volume) were amplified by using the TaqMan Universal PCR Master Mix (Applied Biosystems) to produce PCR products specific for CA125 and TADG-12. Quantitative-RT-PCR was performed with an ABI Prism 7000 Sequence Analyzer using the manufacturer's recommended protocol (Applied Biosystems, Foster City, Calif.) to evaluate expression of CA125 and TADG-12 in primary tumors. Each reaction was run in triplicate. The comparative threshold cycle (CT) method was used for the calculation of amplification fold as specified by the manufacturer. Primers specific for 18S ribosomal RNA and empirically determined ratios of 18S competimers (Applied Biosystems) were used to control for the amount of cDNA generated from each sample. CA125 and TADG12 primers were obtained from Applied Biosystems as assay on demand products (CA125: Assay ID: Hs 00226715-m1; TADG12: Assay ID: Hs 00225161-m1).

Figure 5:
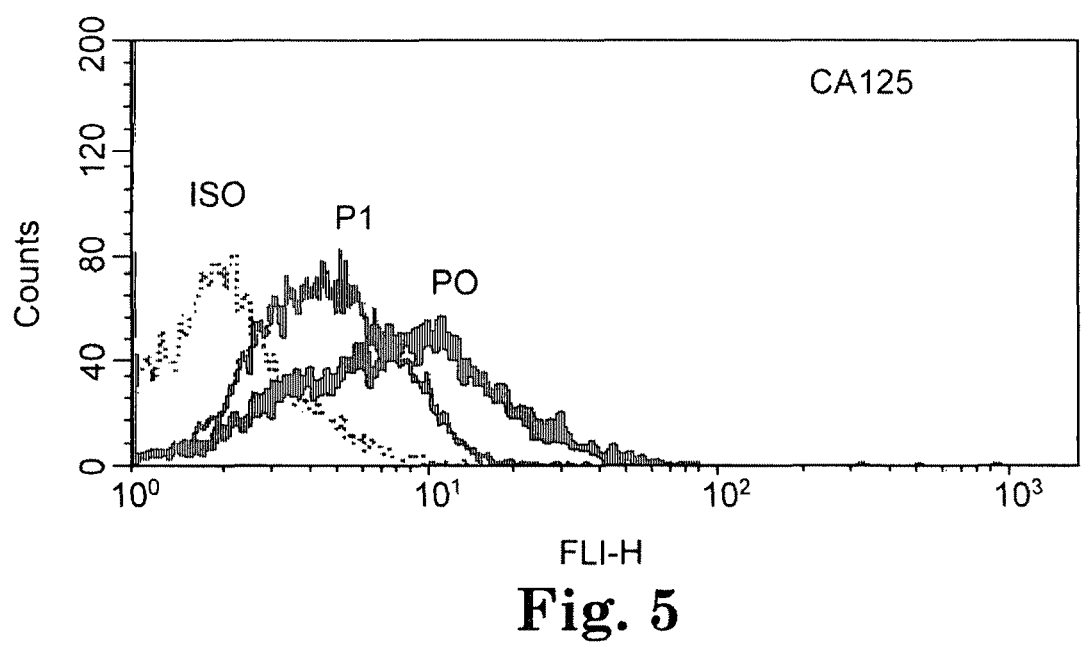
FIG. 5. Representative CA125 expression by flow cytometry on HLA-A2 positive primary ovarian cancer cells from patient 1 used as target in the 5 hr $^{51}$Cr-release cytotoxicity assays shown below. CA125 expression was assessed by flow cytometric staining with OC-125 (Signet Laboratories Inc. Dedham, Mass.) before any in vitro passage (i.e., P0) and after 1 passage of the primary tumor culture in a new flask (i.e., P1).

As shown in FIG. 4 for both CA125 and TADG-12 in patients 1 and 2, we observed a consistent down-regulation of the expression levels of CA125 and TADG-12 in the more advanced in vitro passages of the primary ovarian carcinoma cell lines so far established using real time-PCR. Similar results were obtained for CA125 protein expression using monoclonal antibody specific against CA125 in flow cytometric experiments (FIG. 5). Thus, primary cell lines cultured for several passages in vitro may represent suboptimal models for evaluating the potential of CA125 and TADG12 peptide pulsed-DC stimulated CTL therapy against ovarian cancer. Based on these findings, early passages of primary ovarian cancer cell lines overexpressing CA125 and TADG-12 have been cryopreserved and used in the cytotoxicity assays.

Part 2—CD8+ Cytotoxicity Assay Against Autologous Ovarian Tumor Cells Expressing CA125.

Figure 6:
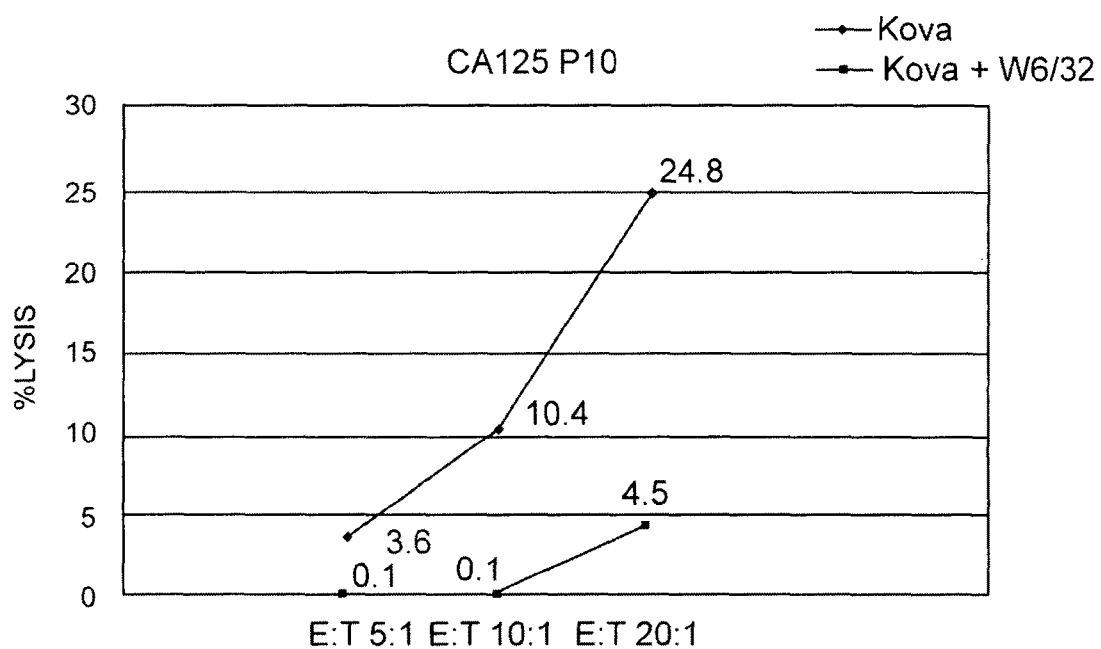
FIG. 6. CD8$^+$ CTL recognition of autologous ovarian cancer cells endogenously expressing CA125 by CA125-P10-stimulated lymphocytes. Cytotoxicity was tested in a 5 hr $^{51}$Cr-release assay against autologous primary ovarian cancer target cells and unpulsed autologous LCL at different Effector cell: Target cell ratios (E:T). Blocking monoclonal antibody (MAb) against non-polymorphic HLA A, B, and C determinants (W6/32) was also used.

Because, CTL cell lines generated by in vitro primary stimulation with high concentration of peptides often fail to lyse targets expressing endogenous antigens (7, 8), we tested the ability of the amplified CA125-peptide-specific CD8+ T cells to lyse autologous HLA-A2+/CA125+ primary ovarian cancer cells as a means to reliably demonstrate specific lysis of targets endogenously expressing antigen. Unlike peptides 7, 11 and 12, only the CA125 YTLDrDSLYV (SEQ ID NO:10) peptide (P10) was found to be reliably cytotoxic against primary ovarian cancer cells endogenously expressing CA125 (FIG. 6). CTL stimulated by P10-pulsed autologous DC were consistently strongly cytotoxic against autologous primary ovarian cancer target cells endogenously expressing CA125, but not against autologous unpulsed LCL (FIG. 6). Moreover, cytotoxicity was significantly inhibited by blocking monoclonal antibody (MAb) against non-polymorphic HLA A, B, and C determinants (W6/32 antibody) ($p<0.05$) (FIG. 6) while natural-killer (NK)-sensitive K562 cells were not lysed (not shown).

Figure 7:
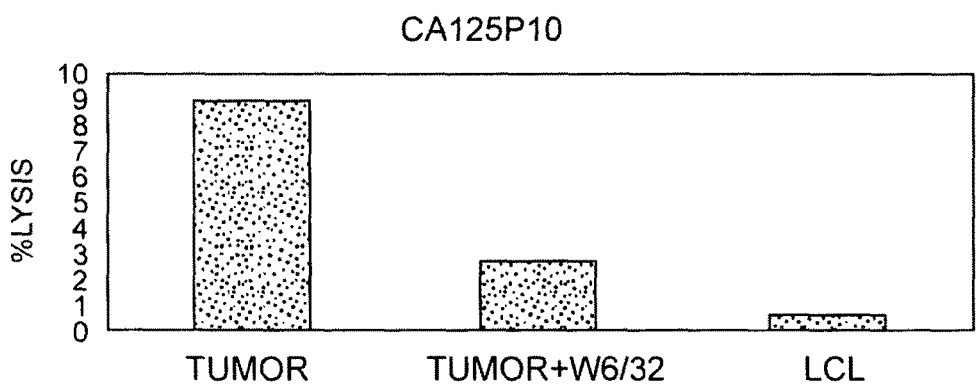
FIG. 7. CD8$^+$ CTL recognition of autologous ovarian cancer cells endogenously expressing CA125 by CA125-P10-stimulated lymphocytes. Cytotoxicity was tested in a 5 hr 5 Cr-release assay against autologous primary ovarian cancer target cells and autologous LCL at a 20:1 ratio. Blocking monoclonal antibody against non-polymorphic HLA A, B, and C determinants (W6/32) was also used. A representative experiment from patient 2 is shown.

FIG. 7 shows the results of a representative experiment obtained with peripheral blood leukocytes from a second HLA-A2 positive patient harboring a CA125-positive tumor. Similarly to patient #1, CTL stimulated by P10-pulsed autologous DC were cytotoxic against autologous primary ovarian cancer target cells endogenously expressing CA125, but not against autologous unpulsed LCL (FIG. 7). Moreover, cytotoxicity was significantly inhibited by blocking monoclonal antibody (MAb) against non-polymorphic HLA A, B, and C determinants (FIG. 7).

Example 10

Cytotoxicity of TADG12-Derived-Peptide-Specific CD8+ T Cells Against Autologous Ovarian Cancer Cells Expressing TADG-12

Cryopreserved peripheral blood leukocytes (PBL) from patient # 3, harboring advanced stage ovarian cancer, have been used for the generation of DC. Monocyte-derived DC were cultured in AIM-V (Gibco-BRL) supplemented with GM-CSF and IL-4 (1). After 5 days' culture, DC maturation was induced by addition of TNFα, IL-1β and PGE$_2$ (1). Mature DC were pulsed for 1-2 hr at 37° C. with 50 µg/ml of all 8 TADG-12-derived peptides, and washed twice before culture with PBL at a responder:stimulator ratio of 30:1. The culture medium was AIM-V plus 5% human AB serum (Gemini Bioproducts). No IL-2 was added. After 7 days, responder T cells were collected and restimulated with peptide-pulsed DC. For the second and third DC stimulations, the medium was supplemented with 50-100 U/ml IL-2, and the culture period extended to 14 days. After the third cycle, CD8+ T cells were recovered by positive selection with anti-CD8 magnetic beads (Dynal). Subsequent restimulations (passages) of CD8+ T cells used peptide-loaded autologous PBL as antigen-presenting cells.

Figure 8:
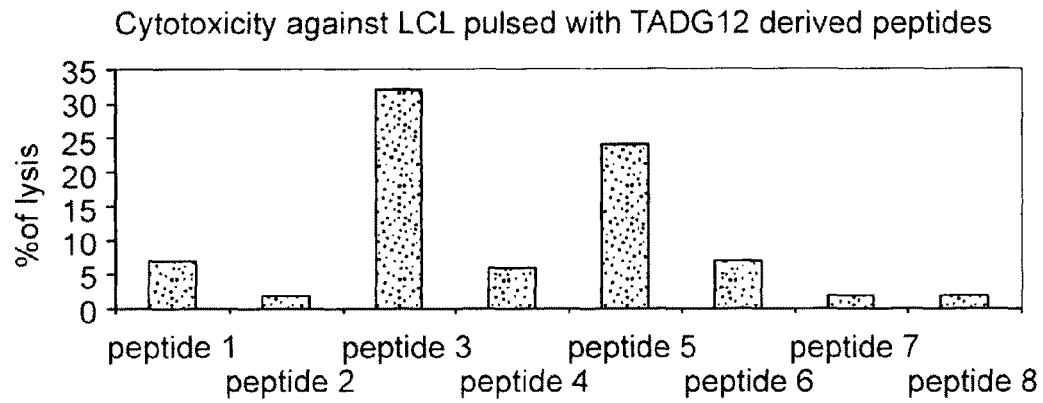
FIG. 8. CD8$^+$ CTL recognition of LCL from patient 1 pulsed with 8 TADG-12-derived peptides. Cytotoxicity was tested in a 5 hr $^{51}$Cr-release assay against autologous LCL and autologous LCL pulsed with 50 μg/ml peptide. Bars represent % cytotoxicity of TADG-12 derived peptide specific CD8+ T cell populations against LCL pulsed with each peptide after subtraction of the cytotoxic activity against LCL controls (i.e., unpulsed). A representative experiment is shown.

As representatively shown in FIG. 8, different levels of cytotoxic responses against peptide-loaded autologous LCL targets were seen from the 4$^{th}$ passage onwards in 8 out of 8 TADG-12 peptides.

Figure 9:
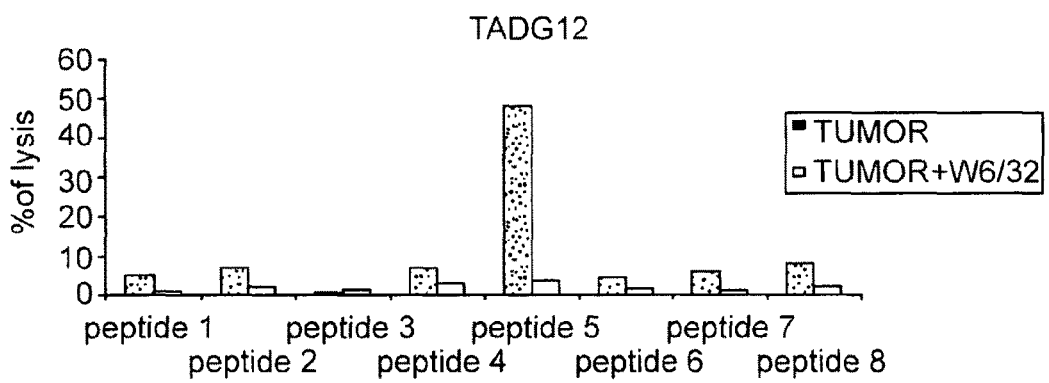
FIG. 9. CD8$^+$ CTL recognition of autologous ovarian cancer cells endogenously expressing TADG-12 by all different populations of TADG-12 peptide pulsed-DC-stimulated lymphocytes. Cytotoxicity was tested in a 5 hr $^{51}$Cr-release assay against autologous primary ovarian cancer target cells at a 20:1 ratio. Blocking monoclonal antibody (MAb) against non-polymorphic HLA A, B, and C determinants (W6/32) was also used. A representative experiment from patient 1 is shown.
Figure 10:
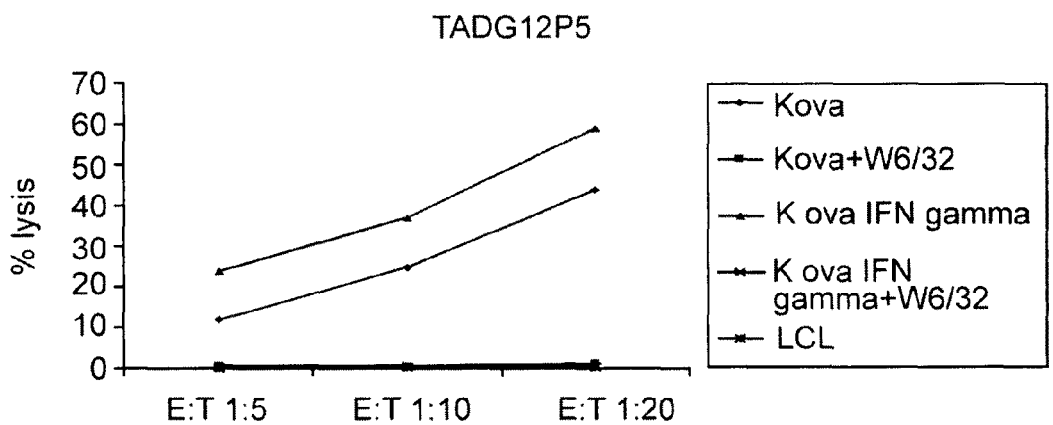
FIG. 10. CD8$^+$ CTL recognition of autologous ovarian cancer cells (i.e., K ova) endogenously expressing TADG-12 by TADG-12 P5-stimulated lymphocytes. Cytotoxicity was tested in a 5 hr $^{51}$Cr-release assay against autologous primary ovarian cancer target cells exposed or not exposed to 500 μg/ml of IFN-γ for 48 hrs and unpulsed autologous LCL at different E:T ratios. Blocking monoclonal antibody (MAb) against non-polymorphic HLA A, B, and C determinants (W6/32) was also used. A representative experiment from patient 1 is shown.

Next, we have used autologous primary ovarian cancer cells expressing TADG-12 as a means to reliably demonstrate specific lysis of targets endogenously expressing antigen. In this regard, with the exception of CD8+ T cells stimulated with TADG-12 peptide #5, all other populations of CTL were found to have low cytotoxicity against TADG-12 positive autologous primary ovarian cancer cells in multiple experiments (FIG. 9). Only the YLPKSWTIQV peptide (i.e., P5) was consistently found strongly cytotoxic against autologous primary ovarian cancer target cells endogenously expressing TADG-12 (FIGS. 9 and 10). Moreover, cytotoxicity was significantly inhibited by blocking monoclonal antibody (MAb) against non-polymorphic HLA A, B, and C determinants while HLA class I identical TADG-12 negative LCL controls were not significantly killed (FIG. 10). Finally, exposure of tumor cells to IFN-γ for 48 hrs further increased recognition and killing of autologous ovarian cancer cells (FIG. 10).

Example 11

T Cell Cytokine Expression and Mechanism of Cytotoxicity

As reported above, DC pulsed with multiple TADG-12 and CA125 derived peptides may induce strong HLA A*0201-restricted cytotoxic responses against autologous LCL pulsed with these peptides as well as against autologous ovarian cancer primary cell lines. In an attempt to identify the mechanisms of CD8+ T cell lysis of CA125- and TADG-12-positive primary ovarian cancer cell lines, we performed flow cytometric analysis of cell surface antigens combined with intracellular cytokine expression (see next section) and perforin level in peptide specific CD8+ T cell populations and autologous tumor cells.

Briefly, tumor cells were harvested with 0.25 percent trypsin in HBBS (Gibco, Grand Island, N.Y.) and washed once in complete medium. Cell suspensions were counted and distributed into 12×75 mm tubes at $5×10^5$ cells/tube. Mouse monoclonal antibodies [anti-HLA class I (MAb W6/32); anti-HLA-A2 (BB7-2) and anti-HLA Class II (MAb CR3-43) Accurate Chemical and Scientific Corporation, Westbury, N.Y.); and anti-ICAM-1 (MAb LB-2; Becton Dickinson)] were diluted in cold assay buffer (PBS, pH 7.2, supplemented with 0.1% FCS) and added in a 50-μl volume. A mouse IgG preparation (MAb IgG2a; Becton Dickinson) was used as negative control. Tumor cells were analyzed by FACScan (Becton Dickinson) utilizing Cell Quest software (Becton Dickinson).

Flow cytometry for cell surface antigen expression by peptide specific CD8+ T cell populations was performed using MAbs directly conjugated against CD8, (Leu-2a, T cytotoxic/suppressor), CD56 (Leu-19, NK/K cells), anti-CD11a/LFA-1 and isotype matched controls (Becton Dickinson, San Jose, Calif.) and analyzed on a FACScan (Becton Dickinson). For evaluation of intracellular perforin, harvested cells were washed and fixed with 2% paraformaldehyde in PBS for 20 min at room temperature. Cells were then washed and permeabilized by incubation in PBS plus 1% BSA and 0.5% saponin (S-7900, Sigma, St. Louis, Mo.) for 10 min at room temperature. CD8+ peptide specific T cell populations were stained with FITC-anti-perforin MAb (Delta G9) (PharMingen, San Diego, Calif.) and isotype-matched control MAb (FITC-anti-Igγ2a) (PharMingen). After staining, cells were washed twice with PBS plus 1% BSA and 0.5% saponin, once with PBS plus 0.5% BSA, and fixed a second time with 2% paraformaldehyde in PBS.

CD11a-ICAM Interactions

Figure 11:
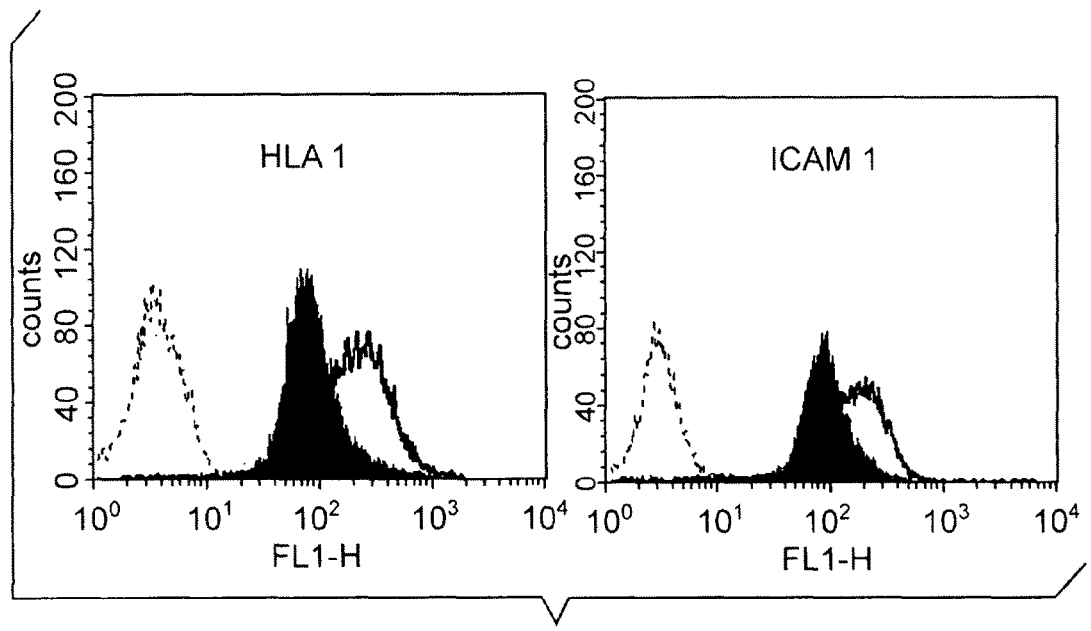
FIG. 11. Flow cytometric analysis of HLA class I and ICAM-1 expression by primary ovarian tumor cells from patient # 3 before and after exposure to IFN-γ. Left panel: HLA class I expression. Right panel: ICAM-1 expression. Solid profiles=HLA class and ICAM-1 expression before IFN-γ exposure; Open profiles=HLA class I and ICAM-1 expression after IFN-γ exposure. Dotted line profiles represent the negative control.

As representatively shown for primary tumor #3, all ovarian tumor cell lines tested in cytotoxicity experiments were found to express significant levels of MHC class I and ICAM-1 molecules (FIG. 11). In contrast, MHC class II molecule expression was negligible in all 3 primary tumor cell lines tested (data not shown). Because exposure to IFN-γ was consistently found to significantly increase the cytotoxic activity of peptide-specific CTL populations against autologous tumor cells overexpressing TADG-12 (FIG. 10), and CA125 (data not shown), we analyzed the effects of IFN-γ exposure to the expression levels of HLA class I, HLA-A2, ICAM-1, TADG-12 and CA 125 by flow cytometry and real time PCR in primary ovarian cancer cells. As representatively shown in FIG. 11, primary tumor cell lines were found to markedly up-regulate MHC class I, HLA-A2 (not shown) and ICAM-1 expression levels after a brief exposure to IFN-γ (i.e., 500 U/ml for 48 hrs) by flow cytometry.

In contrast, in multiple experiments, we did not detect any change in the expression levels of CA125 and TADG-12 mRNA in any of the primary ovarian cancer cell lines tested by real time PCR after exposure to IFN-γ (data not shown).

Figure 12:
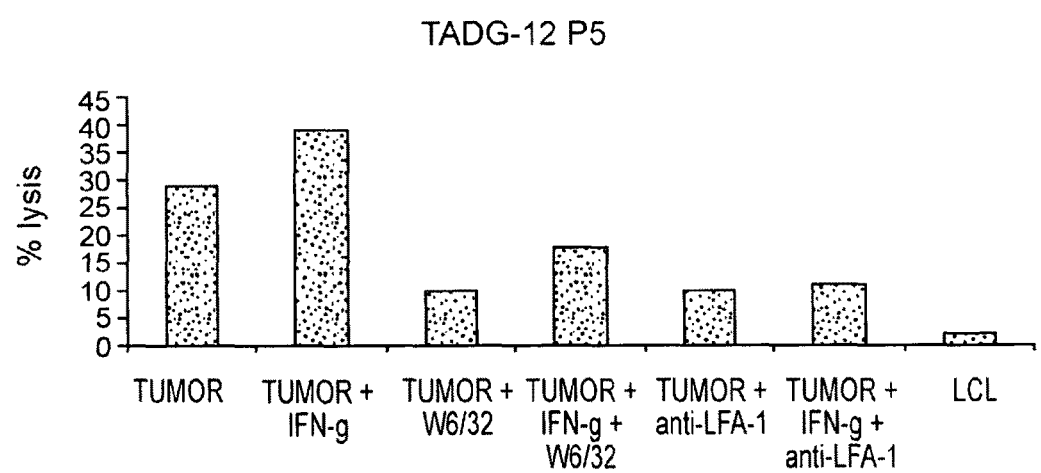
FIG. 12. CD8$^+$ CTL recognition of autologous ovarian cancer cells endogenously expressing TADG-12 by TADG12-P5-stimulated lymphocytes. Cytotoxicity was tested in a hr $^{51}$Cr-release assay against autologous primary ovarian cancer target cells exposed or not exposed to 500 U/ml of IFN-γ for 48 hrs and unpulsed autologous LCL at 20:1 ratios. Blocking monoclonal antibody (MAb) against non-polymorphic HLA A, B, and C determinants (W6/32) and anti-CD11a/LFA-1 were also used. A representative experiment from patient 3 is shown.

Importantly, as representatively demonstrated in FIG. 12, in multiple cytotoxicity assays we found that, in addition to the monoclonal antibody (MAb) against non-polymorphic HLA A, B, and C determinants (W6/32), anti-CD11a (LFA-1) MAb was also able to block tumor lysis by peptide-specific CTLs to a significant extent.

Consistent with this view, in multiple cytotoxicity assays performed on tumor cells after IFN-γ exposure, anti-CD11a (LFA-1) MAb appeared significantly more potent in blocking tumor lysis by peptide specific CTLs when compared to W6/32 MAb, the range of inhibition being from 60 to 86% for anti-CD11a (LFA-1) MAb versus 50 to 76% for W6/32 MAb (p=0.04, FIG. 8). CD11a is the receptor for ICAM, so this indicates that the ICAM adhesion is critical for tumor cell killing by the CTLs.

These findings strongly suggest that CD11a-CD54 adhesion pathway is critical for effective TADG-12 and CA125 peptide specific CD8+ T cell mediated lysis of primary ovarian tumor target cells. Furthermore, altogether these results support the view that the increased killing detected after IFN-γ exposure in primary ovarian tumor cell lines is not related to an increase in the expression levels of CA125 and TADG-12, but to both an upregulation of HLA class I molecules, and to a more significant extent, an increased expression of ICAM-1 adhesion molecule on tumor cells.

Perforin.

Figure 13:
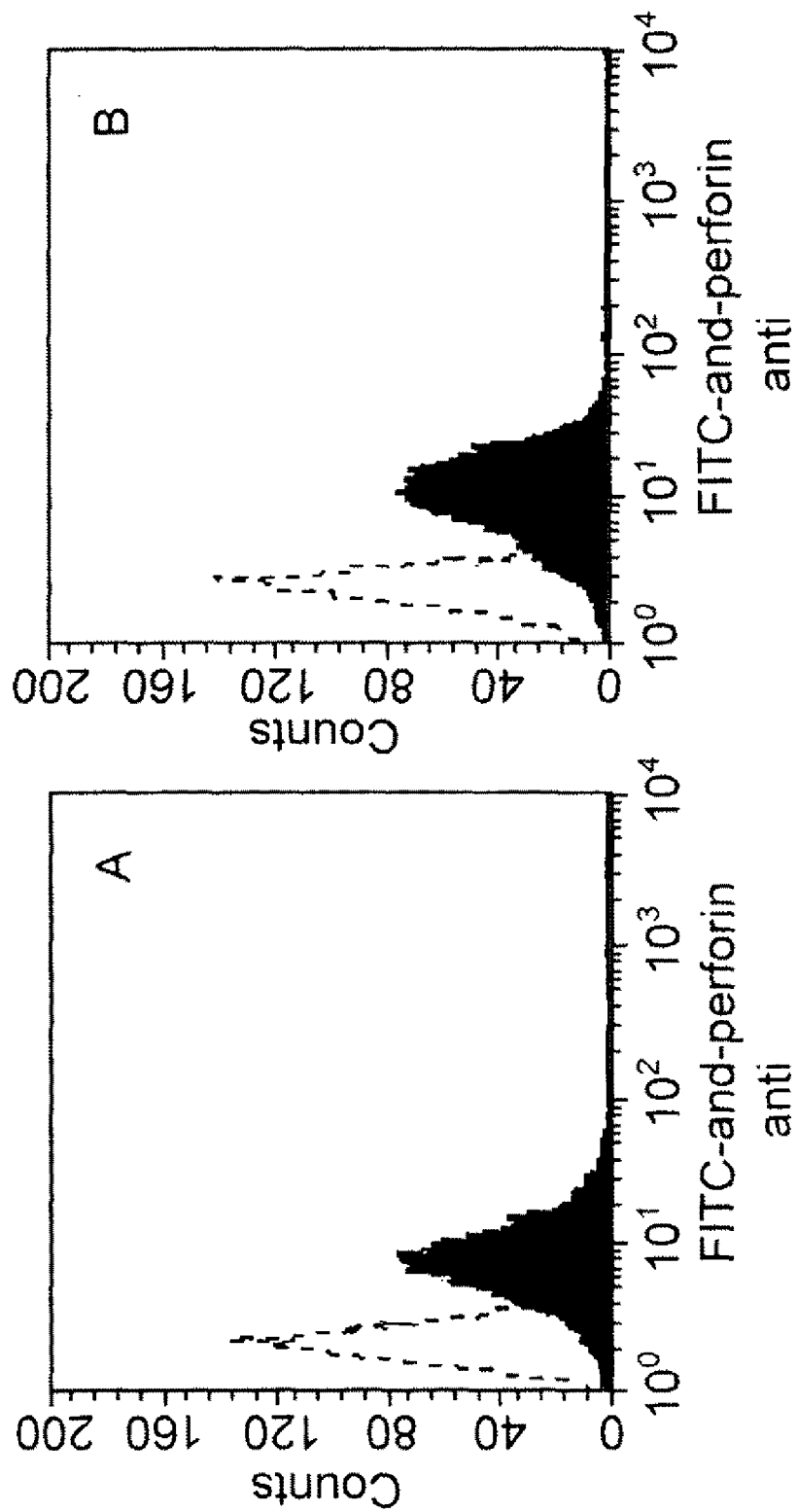
FIG. 13. Flow cytometric analysis of expression of intracellular perform by CA125 P10 (A) and TADG-12 P5 (B) stimulated lymphocytes. Histograms from cells stained with isotype control mAb are shown in dotted lines.

Of interest, when CA125 and TADG-12 peptide-specific CTL were analyzed by flow cytometric analysis for CD56 expression and intracellular perforin levels, we found a significant correlation between high expression of perforin and increased cytotoxic activity against tumor cells. Indeed, as representatively shown in FIG. 13 for CA125 P10 and TADG-12 P5 stimulated lymphocytes, high levels of perforin were consistently detected in both these highly cytotoxic T cell populations. In contrast, low levels of perforin were detected in the majority of the poorly cytotoxic CA125 and TADG-12 peptide-specific T cell populations (data not shown).

CD56.

Finally, no correlation was found between cytotoxicity and CD56 expression in CA125 P10 and TADG-12 P5 stimulated lymphocytes. Indeed, in multiple experiments, only 2% to 4% of the CD8+ T cells from CA125 P10 and TADG-12 P5 stimulated lymphocytes were found to co-express the CD56 marker (data not shown). These results are in contrast with the high expression of CD56 previously reported in Human Papillomavirus 16/18 E7/tumor-specific CD8+ CTLs by our group (4).

Cytokine Expression.

To evaluate whether cytokine expression from CA125 and TADG-12 peptide-stimulated CD8+ T cells segregate in discrete interferon-γ+/interleukin-4— and interferon-γ-/interleukin-4+ subsets we used flow cytometric techniques to detect intracellular cytokine expression at single cell level. In our first analysis we tested intracellular IFN-γ and IL-4 cytokine expression of the CTL populations obtained from patient #3 following antigen stimulation with LCL loaded with TADG-12 and CA125 derived peptides.

Figure 14:
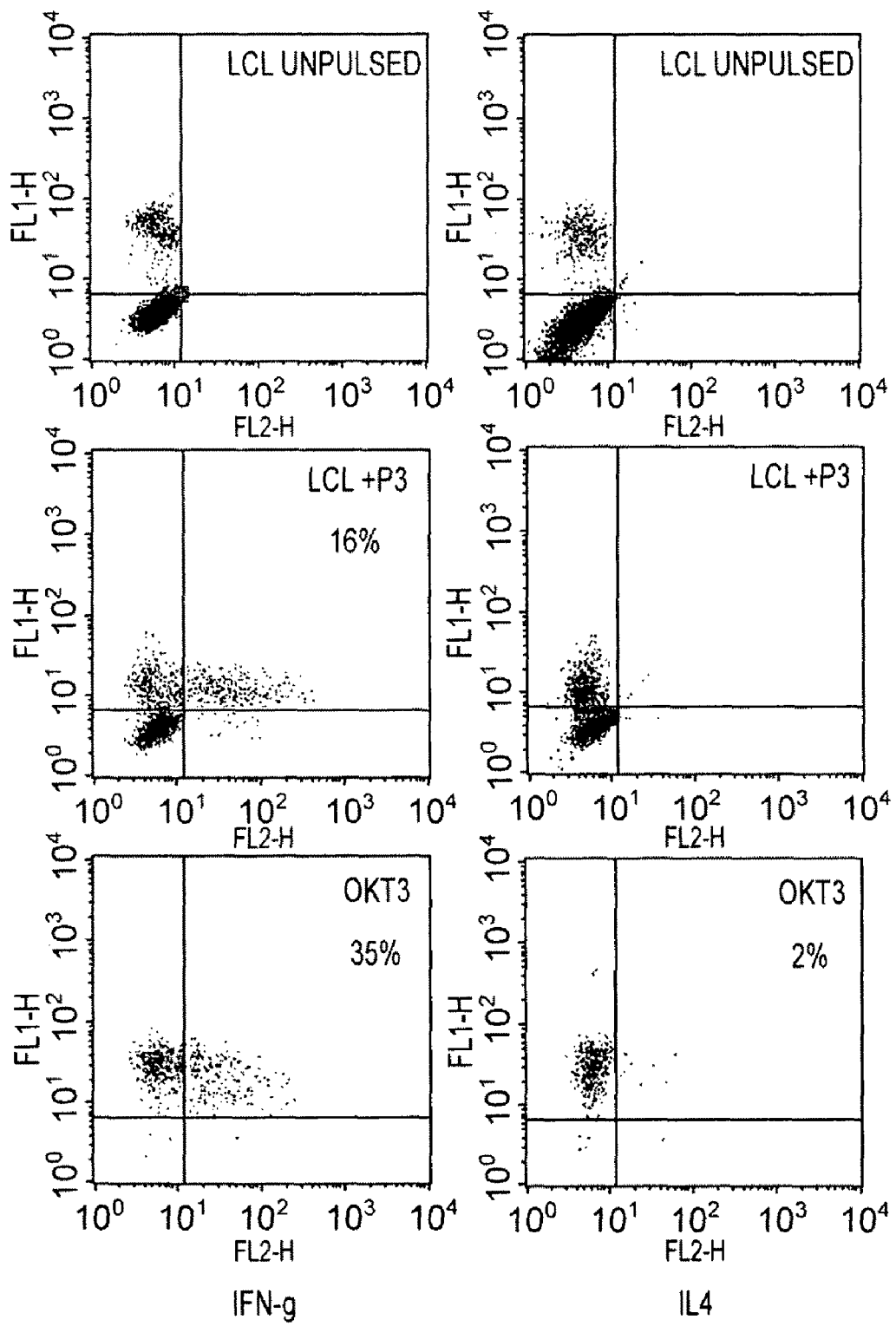
FIG. 14. Distribution of IFNγ-expressing and IL-4-expressing T cells specific against TADG-12 P3 peptide in response to stimulation with unpulsed LCL (negative control, upper panel), P3 peptide-pulsed LCL (middle panel), and solid phase OKT3 antibody (positive control, lower panel), as revealed by flow cytometric analysis of intracellular cytokine expression. A representative experiment from patient 3 is shown.

We found that, although analysis of the frequency of antigen-responsive cells (based on modulation of CD8 expression in response to antigen stimulation, data not shown) demonstrated that most of the T cells were antigen-responsive, only few of these peptide-specific CTL populations were able to secrete significant amounts of IFN-γ after peptide antigen stimulation as detected by flow cytometry. Indeed, as representatively shown for the two most highly cytotoxic TADG-12 peptides P3 and P5, only CTL specific for peptide 3 were able to express high levels of IFN-γ after overnight stimulation with peptide-loaded LCL (FIGS. 14 and 15).

Figure 15:
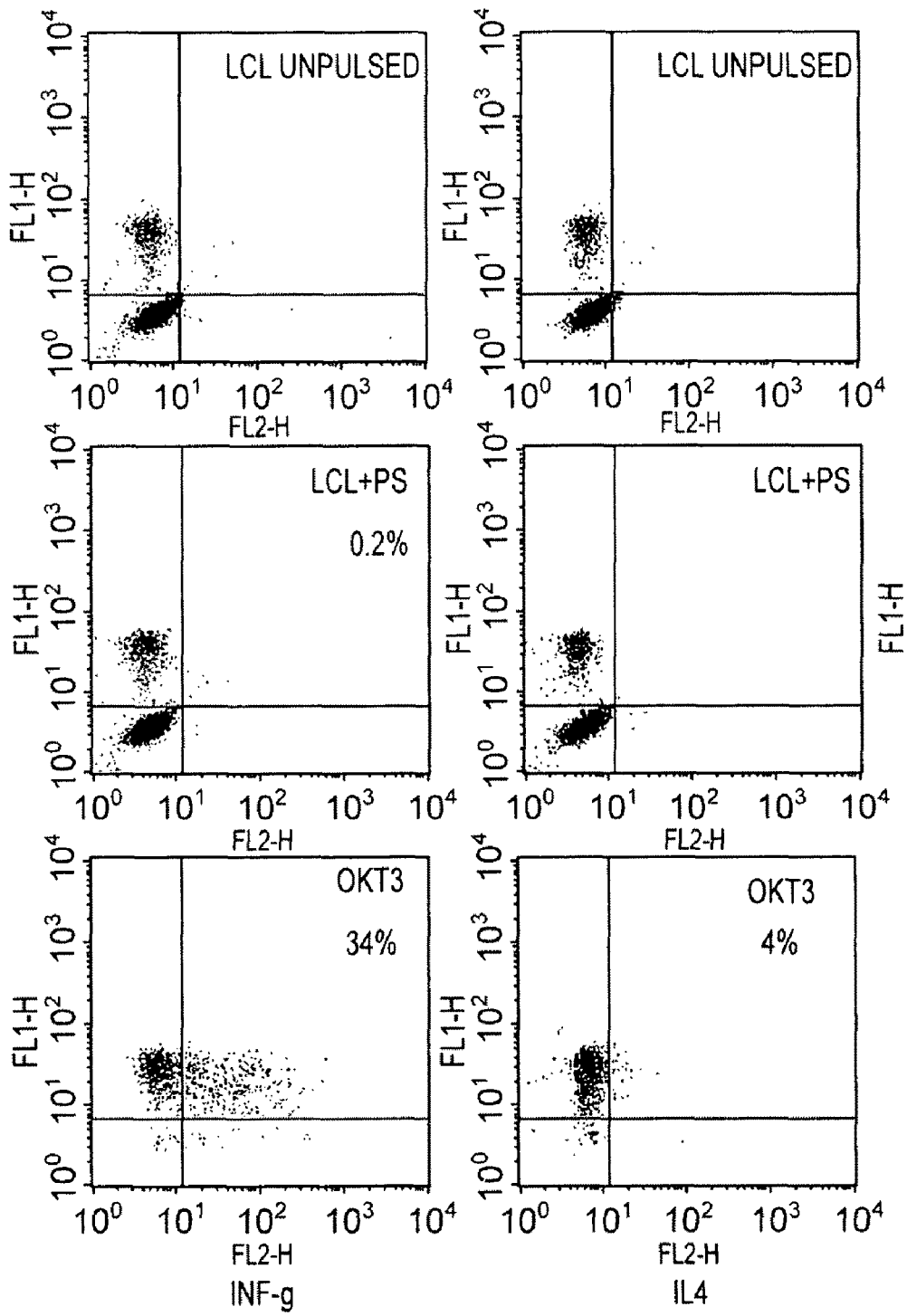
FIG. 15. Distribution of IFNγ-expressing and IL-4-expressing T cells specific against TADG-12 P5 peptide in response to stimulation with unpulsed LCL (negative control upper panel), P5 peptide-pulsed LCL, (middle panel), and solid phase OKT3 (positive control, lower panel), as revealed by flow cytometric analysis of intracellular cytokine expression. A representative experiment from patient 3 is shown.

IFN-γ expression by TADG-12 P5 specific CTL was detected only when stimulated overnight by solid phase OKT-3 (i.e., positive control, FIG. 15). Similar results (i.e., no significant intracellular IFN-γ expression) were obtained when the cytotoxic P10 CA125 peptide specific T cell population was stimulated with autologous P10-loaded LCL overnight (data not shown). Finally, no significant IL-4 secretion was found in any of the TADG-12 and CA125 specific CTL populations studied suggesting no bias in favor of a Type 2 cytokine profile (FIGS. 14 and 15).

We do not have a clear explanation of why the TADG-12 P5 and CA125 P10 peptide-specific CTL populations are unable to secrete high amount of IFN-γ in response to stimulation with the specific peptides. However, from previous studies it is known that different thresholds of T cell receptor stimulation in CTL may induce diverse effector functions. Indeed, while low level of T cell stimulation in primed CD8+ T cells may induce strong cytotoxic responses against the specific target antigen, higher threshold of T cell receptor stimulation may be necessary to induce strong CTL proliferation and/or cytokine release (4). On the basis of these studies as well as our preliminary observations on cytokine secretion derived by flow cytometric data and ELISPOT assays (see below) we are tempted to speculate that TADG-12 P5- and CA125 P10-specific T cell populations may receive too low stimulation from LCL pulsed with TADG-12 P5- and CA 125 P10 peptides to secrete the large amounts IFN-γ necessary for detection by FACS analysis. Nevertheless, these peptide specific T cells are highly cytotoxic against LCL loaded with the specific peptides or against autologous tumor cells endogenously expressing TADG-12 and/or CA125 tumor antigens.

ELISPOT Assays for Cytokine Expression.

ELISPOT is a modification of an ELISA assay to detect cytokine production locally. The surface of a substrate is coated with antibody against the cytokine of interest. Cells are incubated on the substrate under conditions where they may secrete cytokine. Any cytokine secreted will be captured locally by the antibody. After the incubation period, the cells are washed away, and the substrate is incubated with a secondary antibody against the cytokine. The secondary antibody is typically biotinylated and can be visualized by adding streptavidin-alkaline phosphatase reagent. This reagent catalyses the conversion of a substrate to a deep purple stain, causing purple spots to appear wherever an activated T cell was. By counting these spots, we can ascertain what fraction of T cells are be activated by a given antigen.

Figure 16:
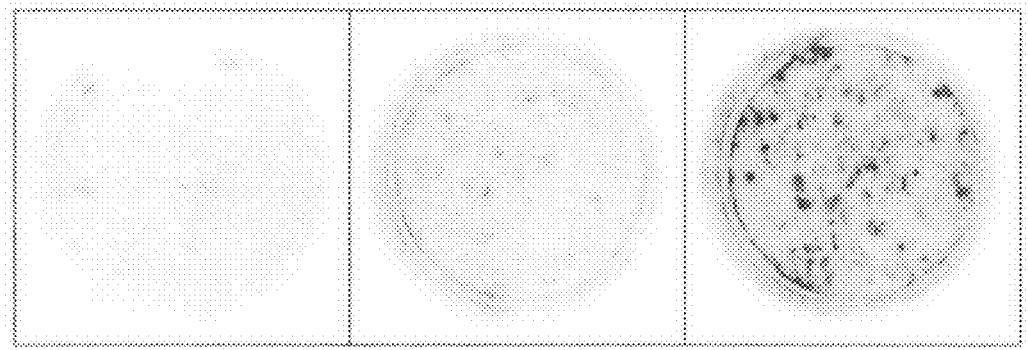
FIG. 16. ELISPOT assay for production of IFNγ by CD8+ T cells specific for TADG-12. PBL were cultured through four rounds of stimulation in vitro with TADG-12 P5 peptide-loaded mature DC. Assays were conducted with purified CD8+ T cells ($10^5$/well) stimulated overnight with DC pulsed with 50 μg/ml peptide. CD8+ T cells stimulated with DC only (left panel, negative control), DC loaded with TADG-12 P5 peptide (middle panel) and activated overnight with OKT3 stimulation (positive control, right panel).

Enumeration of antigen-responsive cells that produce particular cytokines is valuable for functional analysis and quantitation of immune responses, particularly following immunization. Furthermore, the ELISPOT assay offers a technique that is more sensitive than flow cytometry to analyze cytokine expression in peptide specific T cell populations. In this section, results of the use of ELISPOT assay for determination of the frequency of IFNγ-secreting CD8+ T cells specific for TADG-12 and CA125 tumor antigen-loaded DC are described. As representatively shown in FIG. 16 for Patient 3, significant numbers of IFNγ-secreting CD8+ T cells specific against TADG-12 P5 were detected after 4 rounds of restimulation with peptide pulsed DC. OKT3, a monoclonal antibody against the T cell receptor CD3 that activates T cells, was used as a positive control.

Figure 17:
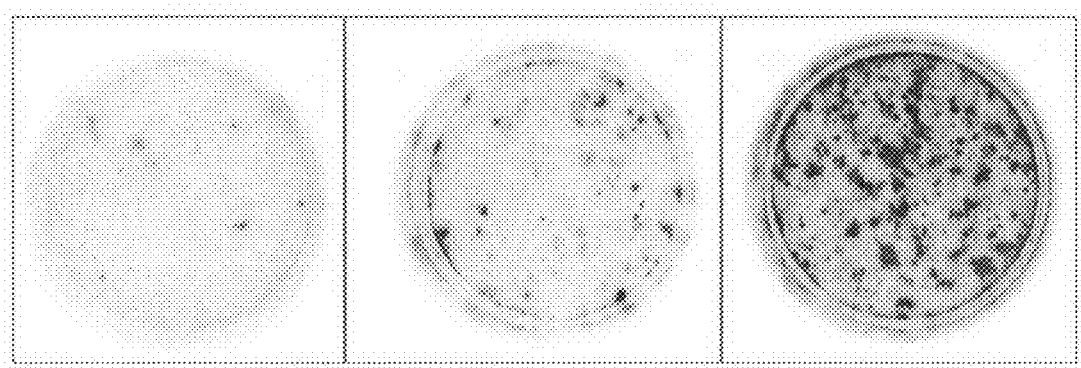
FIG. 17. ELISPOT assay for production of IFNγ by CD8+ T cells specific for CA125. PBL were cultured through four rounds of stimulation in vitro with CA125 P10 peptide-loaded mature DC. Assays were conducted with purified CD8+ T cells ($10^5$/well) stimulated overnight with DC pulsed with 50 µg/ml peptide. CD8+ T cells stimulated with DC only (left panel, negative control), DC loaded with CA125 P10 peptide (middle panel) and activated overnight with OKT3 stimulation (positive control, right panel).

Similarly, analysis of CD8+ T cells specific for CA125 peptide 10 (FIG. 17) suggests that IFNγ ELISPOT assays are more sensitive than flow cytometric analysis of intracellular cytokine expression to detect IFNγ secretion by CA125 P10 specific CTL. Importantly, these data suggest that ELISPOT can be used to monitor the frequency and function of TADG-12 and/or CA125 antigen-specific T cells in clinical trials of tumor vaccines and immunotherapy.

The ELISPOT assays were conducted using IFN-γ ELISPOT kits (BD Biosciences PharMingen, San Diego, Calif.) to determine the frequency of cytokine-expressing in vitro stimulated CD8+ T cells after overnight activation with CA125 or TADG12-peptide-loaded and unloaded stimulator dendritic cells.

Example 12

Infusing Dendritic Cells Loaded with a CA125 Peptide to Treat Ovarian Cancer

Ovarian cancer patients having CA125-positive tumors are treated in this Example. Patients undergo leukopheresis using a COBE separator. Peripheral blood leukocytes (PBL) from the patients are used for generation of dendritic cells (DC). Monocyte-derived DC are cultured in AIM-V (Gibco-BRL) supplemented with GM-CSF and IL-4 (4). After 5 days' culture, DC maturation is induced by addition of TNFα, IL-1β, and $GPE_2$ (4). Mature DC are incubated for 1-2 hours at 37° C. with 50 µg/ml of the peptide P10 (SEQ ID NO:10). The culture medium is AIM-V plus 5% human AB serum (Gemini Bioproducts). No IL-2 is added. The DC are then washed twice to remove unbound peptides. The DC are then suspended in PBS supplemented with 10% autologous serum, and infused intravenously into the patient over a period of one hour.

Patients receive a total of three treatments at two-week intervals.

The treated patients are observed to have less tumor growth, more tumor shrinkage, or longer remissions than comparable patients who do not receive the treatment.

Example 13

Infusing Dendritic Cells Loaded with a TADG-12 Peptide to Treat Ovarian Cancer

Ovarian cancer patients having TADG12-positive tumors are treated in this Example. Patients undergo leukopheresis using a COBE separator. Peripheral blood leukocytes (PBL) from the patients are used for generation of dendritic cells (DC). Monocyte-derived DC are cultured in AIM-V (Gibco-BRL) supplemented with GM-CSF and IL-4 (4). After 5 days' culture, DC maturation is induced by addition of TNFα, IL-1β, and $GPE_2$ (4). Mature DC are incubated for 1-2 hours at 37° C. with 50 µg/ml of the peptide SEQ ID NO:17. The culture medium is AIM-V plus 5% human AB serum (Gemini Bioproducts). No IL-2 is added. The DC are then washed twice to remove unbound peptides. The DC are then suspended in PBS supplemented with 10% autologous serum, and infused intravenously into the patient over a period of one hour.

Patients receive a total of three treatments at two-week intervals.

The treated patients are observed to have less tumor growth, more tumor shrinkage, or longer remissions than comparable patients who do not receive the treatment.

REFERENCES CITED

1. Underwood L J, Shigemasa K, Tanimoto H, Beard J B, Schneider E N, Wang Y, Parmley T H, O'Brien T J. (2000) Ovarian tumor cells express a novel multi-domain cell surface serine protease. *Biochim Biophys Acta* 1502(3): 337-50.
2. O'Brien, T. J., et al. (2002) The CA 125 gene: a newly discovered extension of the glycosylated N-terminal domain structure doubles the size of this extracellular superstructure. Tumor Biol. 23:154-169.

3. Parker, K. C., M. A. Bednarek, and J. E. Coligan. 1994. Scheme for ranking potential HLA-A2 binding peptides based on independent binding of individual peptide sidechains. J. Immunol. 152:163.
4. Santin A D. Hermonat P L. Ravaggi A. Bellone S. Roman J J. Jayaprabhu S. Pecorelli S. Parham G P. Cannon M J. (2001) Expression of CD56 by human papillomavirus E7-specific CD8+ cytotoxic T lymphocytes correlates with increased intracellular perforin expression and enhanced cytotoxicity against HLA-A2-matched cervical tumor cells. *Clin Cancer Res.* 7(3 Suppl):804s-810s.
5. Levitsky V, Zhang Q J, Levitskaya J, Masucci M. G. (1996) The life span of major histocompatibility complex-peptide complexes influences the efficiency of presentation and immunogenicity of two class I-restricted cytotoxic T lymphocyte epitopes in the Epstein-Barr virus nuclear antigen 4. J Exp Med. 183(3):915-26.
6. Torsteinsdottir S, Masucci M G, Ehlin-Henriksson B, Brautbar C, Ben Bassat H, Klein G, Klein E. (1986) Differentiation-dependent sensitivity of human B-cell-derived lines to major histocompatibility complex-restricted T-cell cytotoxicity. Proc Natl Acad Sci USA. 83(15):5620-4.
7. Alexander, M. A., Damico, C. A., Wieties, K. M., Hansen, T. H. and Connolly J. M. (1991) Correlation between CD8 dependency and determinant density using peptide-induced, Ld-restricted cytotoxic T lymphocytes. J. Exp. Med. 173: 849-858.
8. Alexander-Miller, M. A., Leggatt, G. R. and Berzofsky, Y. A. (1996) Selective expansion of high- or low-avidity cytotoxic T lymphocytes and efficacy for adoptive immunotherapy. Proc. Nat. Acad. Sci. USA. 93: 4102-4107.
9. Merogi A J, Marrogi A J, Ramesh R, Robinson W R, Fermin C D, Freeman C M. Tumor-host interaction: analysis of cytokines, growth factors, and tumor infiltrating lymphocytes in ovarian carcinomas. Hum Pathol 1997; 28:321-331.
10. Ioannides C G, Whiteside T L. T cell recognition of human tumors: implications for molecular immunotherapy of cancer. Clin. Immunol. Immunopath. 1993; 66:91-106.
11. Whiteside T L. Tumor infiltrating lymphocytes in human malignancies. Medical Intelligence Unit, R. G. Landes, Austin Tex., 1993.
12. Hirte H, and Clark D A. Generation of lymphokine-activated killer cells in human ovarian carcinoma ascitic fluid: identification of transforming growth factor b as a suppressive factor. Cancer Immuno. Immunother 1991; 32:296-302.
13. Gotlieb W H, Abrams J S, Watson J M, Velu T J, Berek J S, Martinez-Maza O. Presence of IL-10 in the ascites of patients with ovarian and other intra-abdominal cancers. *Cytokine* 1992; 4:385-390.
14. Granger, G., Gatanaga, T., Burger, R., Grosen, E. and DiSaia, P. TNF, LT, and IL-1 natural inhibitors (soluble receptors and receptor antagonists) in women with ovarian cancer. In *Ovarian Cancer* 3: (eds. F. Sharp, W. P. Mason, T. Blackett and J. Berek) Chapman & Hall, London, 1995, pp. 115-119.
15. Santin A D, Hermonat P L, Ravaggi A, Cannon M J, Pecorelli S, and Parham G P. Secretion of vascular endothelial growth factor in ovarian cancer. Eur J. Gynecol. Oncol 1999; 3: 177-181.
16. Rabinowich H, Torsten R E, Kashii Y, Gastman B R, Bell M C, Whiteside T L. Lymphocytes apoptosis induced by Fas-ligand-expressing ovarian carcinoma cells. Implications for altered expression of T cell receptor in tumor associated lymphocytes. J Clin Invest 1998; 101:2579-2588.
17. Loercher A E, Nash M A, Kavanagh J J, Platsoucas C D, Freedman R L. Identification of an IL-10-producing HLA-DR-negative monocyte subset in the malignant ascites of patients with ovarian carcinoma that inhibits cytokine protein expression and proliferation of autologous T cells. J Immunol 1999; 163:6251-6260.
18. Mulders P, Tso C-L, Gitlitz B, Kaboo R, Hinkel A, Frand S, et al. Presentation of renal tumor antigens by human dendritic cells activates tumor infiltrating lymphocytes against autologous tumor: implications for live kidney cancer vaccines. Clin Cancer Res 1999; 5:445-454.
19. Santin A D, Hermonat P L, Ravaggi A, Chiriva-Internati M, Cannon M J, Hiserodt J C, et al. Kinetics of expression of surface antigens during the differentiation of human dendritic cells versus macrophages from monocytes in vitro. Immunobiology 1999; 200:187-204.
20. Steinman R A. The DC system and its role in immunogenicity. Ann. Rev. Immunol. 1991; 9: 271-296.
21. Sallusto F, Lanzavecchia A. Efficient presentation of soluable antigen by cultured human dendritic cells is maintained by granulocyte/macrophage colony stimulating factor plus interleukin 4 and down regulated by turner necrosis factor alpha. J Exp Med 1994; 17:1109-1116.
22. Romani N, Gruner S, Brang D, Kampgen E, Lnez A, Trockenbacher B, et al. Proliferating dendritic cell progenitors in human blood Journal of Experimental Medicine. 1994; 180:83-90.
23. Young J W, Inaba K. DCs as adjuvants for class I major histocompatibility complex-restricted antitumor immunity. J Exp Med 1996; 183:7-11.
24. Schuler G, Steinman R M. Dendritic cells as adjuvants for immune-mediated resistance to tumors. J Exp Med 1997; 186:1183-1187.
25. Banchereau J, Steinman R M. Dendritic cells and the control of immunity. Nature 1998; 392:245-252.
26. Jonuleit H, Kuhn U, Muller G, Steinbrink K, Pragnik L, Schmitt, E, et al. Pro-inflammatory cytokines and prostaglandins induce maturation of potent immunostimulatory dendritic cells under fetal calf serum-free conditions. Eur J Immunol 1997; 27:3135-3142.
27. Dhodapkar M V, Steinman R M, Sapp M, Desai H, Fossella C, Krasovsky J, et al. Rapid generation of broad T-cell immunity in humans after a single injection of mature dendritic cells. J Clin Invest 1999; 104:173-180.
28. Dhodapkar M V, Krasovsky J, Steinman R M, Bhardwaj N. Mature dendritic cells boost functionally superior CD8+ T-cell in humans without foreign helper epitopes. J Clin Invest 2000; 105:R9-R14.
29. Hsu F J, Benike C, Fagnoni F Liles T M, Czerwinski D, Taidi B, et al. Vaccination of patients with B-cell lymphoma using autologous antigen-pulsed dendritic cells. Nature Med 1996; 2:52-58.
30. Geiger J D, Hutchinson R J, Hohenkirk L F, McKenna E A, Yanik G A, Levine J E, et al. Vaccination of pediatric solid tumor patients with tumor lysate-pulsed dendritic cells can expand specific T cells and mediate tumor regression. Cancer Research. 2001; 61:8513-8519.
31. Mellman, I. et al., 2001, Dendritic cells: specialized antigen-presenting machines. Cell 106: 255-258.
32. O'Brien, T. J. et al., U.S. patent application Ser. No. 10/715,066.

All cited patents, patent applications, and other references are incorporated by reference.

What is claimed is:

1. A method of treating cancer in a patient whose cancer cells express CA125 comprising:
   (a) contacting dendritic cells with a purified peptide comprising an HLA-binding CA125 peptide of 7-12 amino acid residues to generate peptide-loaded dendritic cells;
   (b) contacting the peptide-loaded dendritic cells with T cells of the cancer patient to amplify CD8+ T cells that recognize the CA125 peptide; and
   (c) contacting the amplified CD8+ T cells with CA125-bearing cancer cells in the patient to lyse the CA125-bearing cancer cells;
   wherein the CA125 peptide binds to a human class I HLA protein,
   wherein when the CA125 peptide is bound to the HLA protein on the surface of dendritic cells to generate peptide-loaded dendritic cells, and the peptide-loaded dendritic cells are contacted with T cells, the peptide-loaded dendritic cells amplify CD8+ T cells that lyse autologous cells expressing CA125 in vivo or in vitro;
   wherein the purified peptide comprises SEQ ID NO:7, SEQ ID NO:10, SEQ ID NO:11, or SEQ ID NO:12;
   wherein the purified peptide is 7 to 50 amino acid residues in length.

2. The method of claim 1 wherein step (a) is performed ex vivo, step (b) comprises infusing the peptide-loaded dendritic cells into the patient to amplify the CD8+ T cells in vivo in the patient, and step (c) occurs in vivo in the patient.

3. The method of claim 1 wherein steps (a) and (b) are performed ex vivo, and step (c) comprises infusing the amplified CD8+ T cells into the patient to contact the CA125-bearing cancer cells in vivo in the patient.

4. The method of claim 1 wherein the purified peptide is 7 to 12 amino acid residues in length.

5. The method of claim 4 wherein the purified peptide is 8 to 10 amino acid residues in length.

6. The method of claim 1 wherein the purified peptide comprises SEQ ID NO:10 (YTLDRDSLYV).

7. The method of claim 1 wherein the CA125-bearing cancer cells are ovarian cancer cells.

8. The method of claim 1 wherein the CA125-bearing cancer cells are lymphoma cells.

9. A method of treating cancer in a patient whose cancer cells express CA125 comprising:
   (a) contacting dendritic cells with a purified peptide comprising an HLA-binding CA125 peptide of 7-12 amino acid residues to generate peptide-loaded dendritic cells;
   (b) contacting the peptide-loaded dendritic cells with T cells of the cancer patient to amplify CD8+ T cells that recognize the CA125 peptide; and
   (c) contacting the amplified CD8+ T cells with CA125-bearing cancer cells in the patient to lyse the CA125-bearing cancer cells;
   wherein the CA125 peptide binds to a human class I HLA protein,
   wherein when the CA125 peptide is bound to the HLA protein on the surface of dendritic cells to generate peptide-loaded dendritic cells, and the peptide-loaded dendritic cells are contacted with T cells, the peptide-loaded dendritic cells amplify CD8+ T cells that lyse autologous cells expressing CA125 in vivo or in vitro;
   wherein the purified peptide comprises at least 7 amino acid residues of SEQ ID NO:10 in the same order and with the spacing as in SEQ ID NO:10;
   wherein the purified peptide is 7 to 50 amino acid residues in length.

10. The method of claim 9 wherein the purified peptide comprises at least 8 amino acid residues of SEQ ID NO:10 in the same order and with the spacing as in SEQ ID NO:10.

11. The method of claim 9 wherein the purified peptide comprises at least 9 amino acid residues of SEQ ID NO:10 in the same order and with the spacing as in SEQ ID NO:10.

12. The method of claim 9 wherein step (a) is performed ex vivo, step (b) comprises infusing the peptide-loaded dendritic cells into the patient to amplify the CD8+ T cells in vivo in the patient, and step (c) occurs in vivo in the patient.

13. The method of claim 9 wherein steps (a) and (b) are performed ex vivo, and step (c) comprises infusing the amplified CD8+ T cells into the patient to contact the CA125-bearing cancer cells in vivo in the patient.

14. The method of claim 9 wherein the purified peptide is 7 to 12 amino acid residues in length.

15. The method of claim 9 wherein the purified peptide is 8 to 10 amino acid residues in length.

16. The method of claim 9 wherein the CA125-bearing cancer cells are ovarian cancer cells.

17. The method of claim 9 wherein the CA125-bearing cancer cells are lymphoma cells.

\* \* \* \* \*